(12) United States Patent
Desai et al.

(10) Patent No.: US 11,561,387 B2
(45) Date of Patent: Jan. 24, 2023

(54) ENDOSCOPE DESIGNS AND METHODS OF MANUFACTURE

(71) Applicant: Integrated Endoscopy, Inc., Irvine, CA (US)

(72) Inventors: Siddharth Balvantrai Desai, Tustin, CA (US); Kais Almarzouk, Irvine, CA (US); Giuseppe Sacca, Carlsbad, CA (US)

(73) Assignee: Integrated Endoscopy, Inc., Irvine, CA (US)

( * ) Notice: Subject to any disclaimer, the term of this patent is extended or adjusted under 35 U.S.C. 154(b) by 0 days.

(21) Appl. No.: 17/199,321

(22) Filed: Mar. 11, 2021

(65) Prior Publication Data
US 2021/0373316 A1 Dec. 2, 2021

Related U.S. Application Data

(60) Provisional application No. 62/988,881, filed on Mar. 12, 2020.

(51) Int. Cl.
*G02B 23/24* (2006.01)
(52) U.S. Cl.
CPC ..... *G02B 23/2461* (2013.01); *G02B 23/2453* (2013.01); *G02B 23/2484* (2013.01); *G02B 23/243* (2013.01)
(58) Field of Classification Search
USPC .......................................................... 48/68
See application file for complete search history.

(56) References Cited

U.S. PATENT DOCUMENTS

| 4,407,273 | A | * | 10/1983 | Ouchi | A61B 1/00098 |
| | | | | | 600/107 |
| 5,633,754 | A | | 5/1997 | Hoogland | |
| 7,063,663 | B2 | | 6/2006 | Kazakevich | |
| 7,976,462 | B2 | | 7/2011 | Wright et al. | |
| 8,858,425 | B2 | | 10/2014 | Farr et al. | |
| 10,357,149 | B2 | | 7/2019 | Hoyle et al. | |

(Continued)

FOREIGN PATENT DOCUMENTS

| JP | 2017500997 A | * | 1/2017 | ............... A61B 1/00 |
| JP | 2017047173 A | * | 3/2017 | ......... A61B 1/00018 |
| WO | WO 97-27798 A1 | | 8/1997 | |

OTHER PUBLICATIONS

PCT/ISA/210 International Search Report and Written Opinion, PCT/US2021/021999 dated Jun. 29, 2021.

*Primary Examiner* — Behrooz M Senfi
(74) *Attorney, Agent, or Firm* — Knobbe, Martens, Olson & Bear, LLP

(57) ABSTRACT

Various embodiments comprise endoscopes (e.g., arthroscopes) for viewing inside a cavity of a body. The endoscopes may include a tip, at least one solid-state emitter such as light emitting diode (LED), located at the distal end of the endoscope, an elongated member. The elongated member may include a plurality of lenses for transmitting light received from the tip member and an elongated conducting member for providing electric power to the solid-state emitter. The elongated conducting member may include conducting lines embedded in a flexible elongated insulating membrane. The tip member and the elongated member may be configured to dissipate heat generated by the solid-state emitter.

15 Claims, 13 Drawing Sheets

(56) References Cited

U.S. PATENT DOCUMENTS

| | | | |
|---|---|---|---|
| 2002/0166946 A1* | 11/2002 | Iizuka | A61B 1/00172 250/201.2 |
| 2003/0018238 A1 | 1/2003 | Obata et al. | |
| 2003/0120129 A1 | 6/2003 | Nakamura | |
| 2003/0191363 A1* | 10/2003 | Boll | A61B 18/24 600/101 |
| 2006/0041193 A1 | 2/2006 | Wright | |
| 2006/0058584 A1* | 3/2006 | Hirata | A61B 1/00177 600/179 |
| 2007/0088203 A1* | 4/2007 | Lau | A61B 17/0218 600/205 |
| 2011/0092772 A1 | 4/2011 | Weber | |
| 2011/0292195 A1 | 12/2011 | Dahmen | |
| 2011/0306834 A1 | 12/2011 | Schrader | |
| 2013/0184525 A1 | 7/2013 | Kojima | |
| 2013/0331730 A1 | 12/2013 | Fenech | |
| 2018/0092513 A1 | 4/2018 | Melsheimer | |

\* cited by examiner

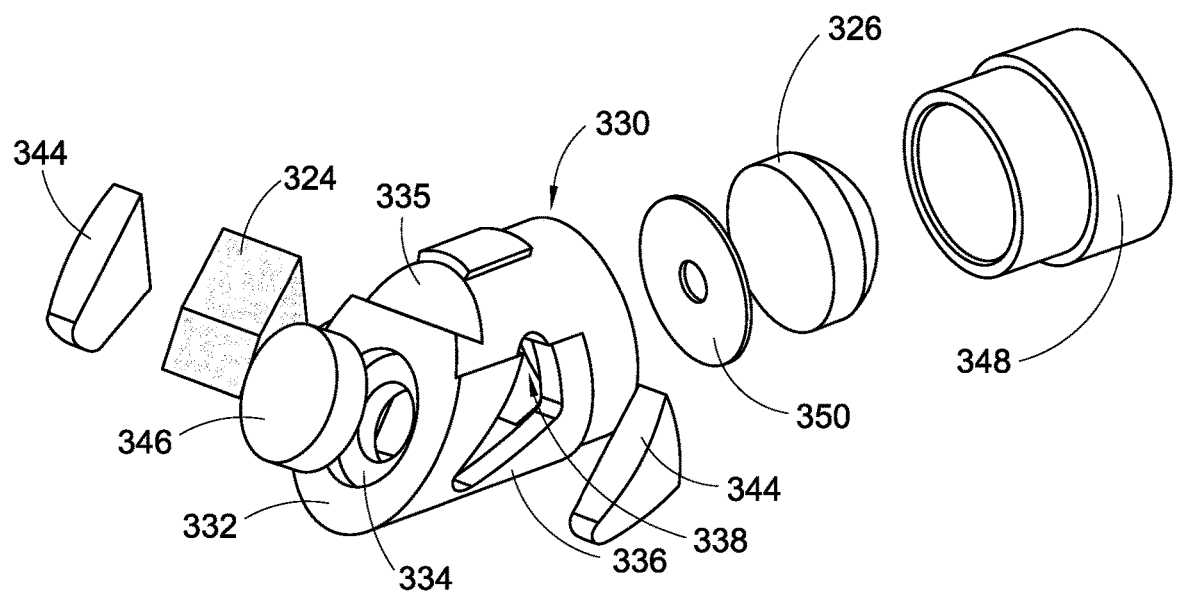
FIG. 3A
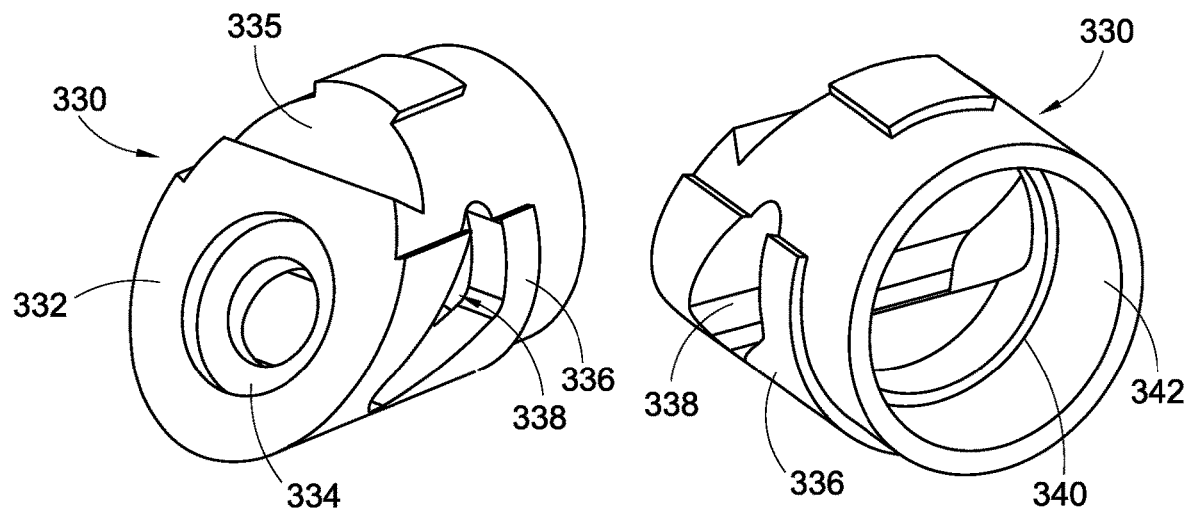
FIG. 3B
FIG. 3C

ENDOSCOPE DESIGNS AND METHODS OF MANUFACTURE

INCORPORATION BY REFERENCE TO ANY PRIORITY APPLICATIONS

This application claims the benefit under 35 U.S.C. § 119(e) of U.S. Provisional Application No. 62/988,881 filed on Mar. 12, 2020 titled "ENDOSCOPE DESIGNS AND METHODS OF MANUFACTURE", which is incorporated herein by reference in its entirety.

This Application is also related to U. S. application Ser. No. 11/099,435 filed on Apr. 5, 2005, now U.S. Pat. No. 7,976,462, and U.S. application Ser. No. 14/567879 filed on Dec. 11, 2014, now U.S. Pat. No. 10,357,149 which are also incorporated by reference herein in their entirety.

BACKGROUND

Field of the Invention

The present invention relates generally to optical systems, and in some embodiments, to endoscopes, arthroscopes, and other medical imaging devices.

Description of the Related Art

Endoscopes such as rigid endoscopes, generally include a tube with imaging optics to be inserted into a cavity in patient's body. Illumination for imaging may be provided by sources that are located external to the patient. Light, for example, from the illumination source may travel via a conduit, such as a fiber-optic or fiber-optic bundle, through the tube into the said cavity. Alternatively, however, illumination may be provided by one or more sources that can be located near the section of the endoscope that is inserted inside a cavity of a body. Light emitting diodes (LEDs) for example, can be mounted at the distal end of the endoscope. In either case, light may illuminate the said cavity at the tube's distal end near a treatment or viewing site. Features inside the cavity of the patient's body can thereby be illuminated and viewed using the imaging optics, which collect light reflected from anatomical features inside the body and form images thereof. Since endoscopes can provide images of anatomical features within the patient's body, endoscopes are useful diagnostic tools.

SUMMARY OF THE INVENTION

Example endoscopes designs are discussed herein. These endoscopes may have one or more advantages that may include, for example, good image quality, low power consumption, and increased ease of fabrication, which can reduce cost of manufacture, and may be portable and/or disposable.

The systems, methods and example embodiments of this disclosure each have several innovative aspects, no single one of which is solely responsible for the all of the desirable attributes disclosed herein. Details of one or more implementations of the subject matter described in this specification are set forth in the accompanying drawings and the description below.

Certain aspects of the present disclosure relate to an endoscope for imaging a target region within a body. The endoscope may comprise a tip member. The tip member may comprise one or more light emitting devices configured to direct illumination at least a portion of said target region.

The tip member may further comprise a front window disposed so as to receive light from said target region when said tip is in said body, and a prism for redirecting light transmitted through said front window. In some implementations, the tip member comprises a housing that supports said one or more light emitting devices and said prism, and the said housing may have a shape that is similar to that of a cross-section of said prism and may comprise copper, a copper alloy, brass or bronze.

The endoscope may further comprise an elongated member having proximal and distal end were the tip member is located. A plurality of lenses may be disposed along an optical path in said elongated member so as to receive light from said prism that is transmitted through said front window.

In certain implementations, the endoscope may include an elongated conducting member comprising a plurality of conducting lines embedded in an insulating membrane disposed along said elongated member. Said elongated conducting member may have a length, width and thickness, wherein said length may be larger than said width and said width may be larger than said thickness. In some such embodiments, said elongated conducting member may comprise a flexible elongated conducting member configured to bend along its length and/or its width. In some cases, said elongate conducting member may have a curved cross-section across its width. In some such cases, elongated conducting member and said insulating membrane may be configured to maintain a curved cross-section across their width when any bending force is removed.

In some examples, said light emitting device may be disposed on said elongated conducting member. In some examples, the said light emitting device may be embedded in said insulating membrane. In some such examples, said light emitting device may be positioned at said distal end of said elongated conducting member. In yet other examples, said light emitting device may have a portion that is not covered by said insulating membrane.

In some implementations, said tip member may comprise a housing having a light emitting device seat, and said light emitting device may be disposed on said light emitting device seat. In some such implementations, said housing may have a shape that is similar to that of a cross-section of said prism and said tip member may have a sidewall with a first opening for inserting said prism.

BRIEF DESCRIPTION OF THE DRAWINGS

In the following description of the various embodiments, reference is made to the accompanying drawings which form a part hereof, and in which is shown by way of illustration various embodiments of the device.

It is to be understood that other embodiments may be utilized and structural changes may be made without departing from the scope of present invention.

FIG. 3A is an exploded view showing different components included in a tip or tip member of the insert portion, the tip member includes a housing configured to support a light source for illuminating a cavity inside the patient as well as optical components for collecting light reflected from anatomical features within the cavity.

FIG. 3B is a perspective view showing the front of the housing of the tip member.

FIG. 3C is a perspective view showing the back of the housing of the tip member.

FIG. 4E shows the light emitting conductive member before and after being disposed on the lens tube and the tip member.

DETAILED DESCRIPTION OF THE PREFERRED EMBODIMENT

Figure 1A:
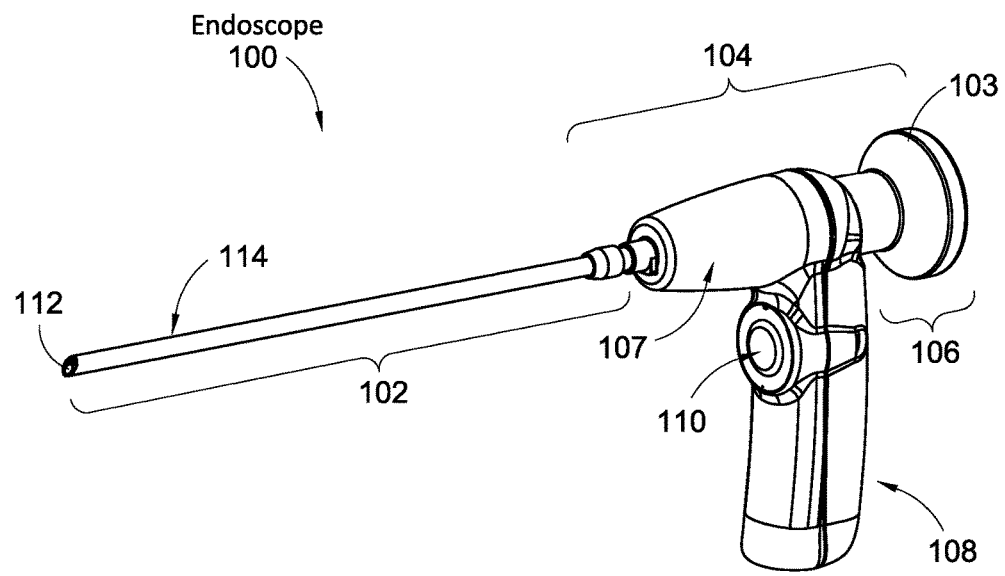
FIG. 1A is a three-dimensional perspective view of an example endoscope comprising a handle portion connected to an insert portion for insertion into a patient's body.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied using a variety of techniques including techniques that may not be described herein but are known to a person having ordinary skill in the art. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Endoscopes for viewing inside the body (also referred to as "target region" herein) are disclosed herein. In some cases, these endoscopes may be inserted inside a cavity of the body to provide images of anatomical features inside the body. Some of these endoscopes may be handheld and possibly portable and/or disposable in some cases, although are not limited thereto. One example of such an endoscope is an arthroscope although the concepts disclosed herein may be applicable to other types of endoscopes as well. Other types of endoscopes may include, ENT (ear, nose and throat) scope, spine scope, and laparoscope, and the like.

These endoscopes can include an optical path from the target region to an eyepiece or ocular such that the user can see an image of a target region. The endoscopes may include one or more light sources that are configured, sized and positioned so as to be inserted into the body cavity to provide illumination therein. In various embodiments, this light source comprises at least one solid state light emitting device such as a light emitting diode (LED). This light emitter may be a small yet bright source of illumination. The light emitter may be powered and/or controlled through power lines such as a conductive member (e.g., elongate conductive member) that provides electrical connection between the light emitter and a power source. The power source can be an external power source (e.g., a power adapter or power supply) or an internal source (e.g., batteries) enclosed in endoscope (e.g., inside its handle portion). In some designs, the intensity of light generated by the light emitter may be controlled by adjusting the power provided to the light emitter using electronic circuitry enclosed in the endoscope (e.g., inside its handle portion).

As discussed above, light emitted from the light sources reflects off anatomical features such walls in the interior of the body cavity or other objects or features therein. A portion of the reflected light is collected through a window or lens in the distal portion of the endoscope and more particularly at the distal end of an elongate insertable portion of the endoscope. In some designs, the window may be angled obliquely with respect to the length of the endoscope (e.g., with respect to the elongate insertable portion of the endoscope) to collect light rays at oblique angles with respect to the endoscope (e.g., the elongate insertable portion of the endoscope). Light collected is then directed along the an optical path through the endoscope, e.g., through the elongate insertable portion of the endoscope, so as to form an image of the anatomical features in the body such as the walls of the cavity or features therein or thereon at the proximal end of the endoscope. In particular, the light may be directed to an eyepiece where an image of the objects or walls can be viewed. In certain designs, the optical path includes a series of lenses such as rod lenses disposed in the elongate insertable portion of the endoscope.

Figure 1B:
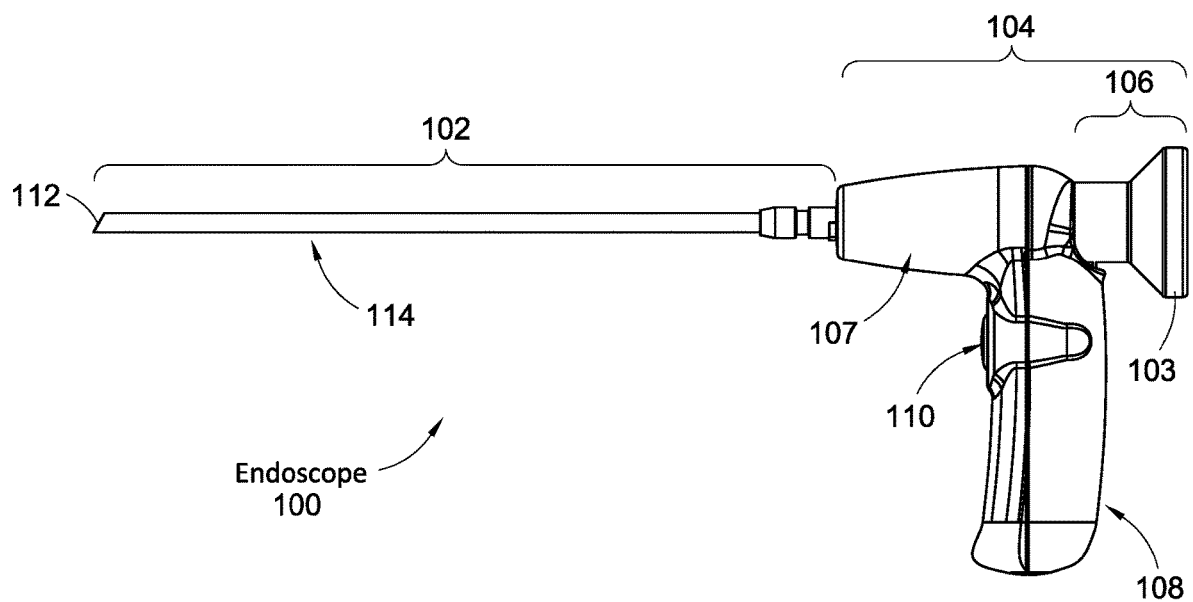
FIG. 1B is a side-view of the endoscope of FIG. 1.

FIGS. 1A and 1B illustrate an example endoscope for providing an image of the target region inside the patient's body. In this example, the endoscope is a battery operated and hand-held instrument that is designed for improved ease of manufacturability. Due to the lower cost of manufacturing, the instrument may also be a disposable instrument. The endoscope 100 compromises a handle portion 104 and an insert portion 102. The insert portion 102 that includes an elongated member 114 and a tip member 112, can be inserted into the body of a patient. The handle portion 104 may include a view port 106, a grip section 108, and an optical joint section 107 for connection with the inert portion 102. The view port 106 may include an eyepiece or ocular lens (not shown) and an eye cup 103 through which the image of the target region can be observed. The optical joint section 107 provides optical and mechanical connection between the insert portion 102 and the handle 104 portion and view port 106. The optical joint section 107 may include a support structure for optical alignment of the proximal end of the elongated member 114 and lenses therein to the view port 106. The grip section 108 provides the ability of the physician to manipulate the endoscope with ease, tilting or rotating the elongated member 114 to image the desired target region inside the patient's body. The grip section 108 of the handle portion may also include an electric compartment that houses batteries and/or electronic circuits. The grip section may also include a user interface 110 (e.g., one or more dials, switches, and/or buttons), for example, for controlling the brightness of the light emitters and adjusting the image sharpness. The insert portion 102 includes a tip member 112, that illuminates the target region and captures the reflected light. The tip member 112 may include one or more light emitters and house optical components to collect light emitted or reflected from the target region. The elongated member 114 guides the captured light to the view port 106, where an image is viewable. The elongated member 114 has a distal end that is connected to the tip member 112 and a proximal end that is inserted into the optical joint section 107. The elongated member 114 may house one or more optical elements (e.g., rod lenses) to guide light from the tip member 112 to the optical joint 107.

Figure 2:
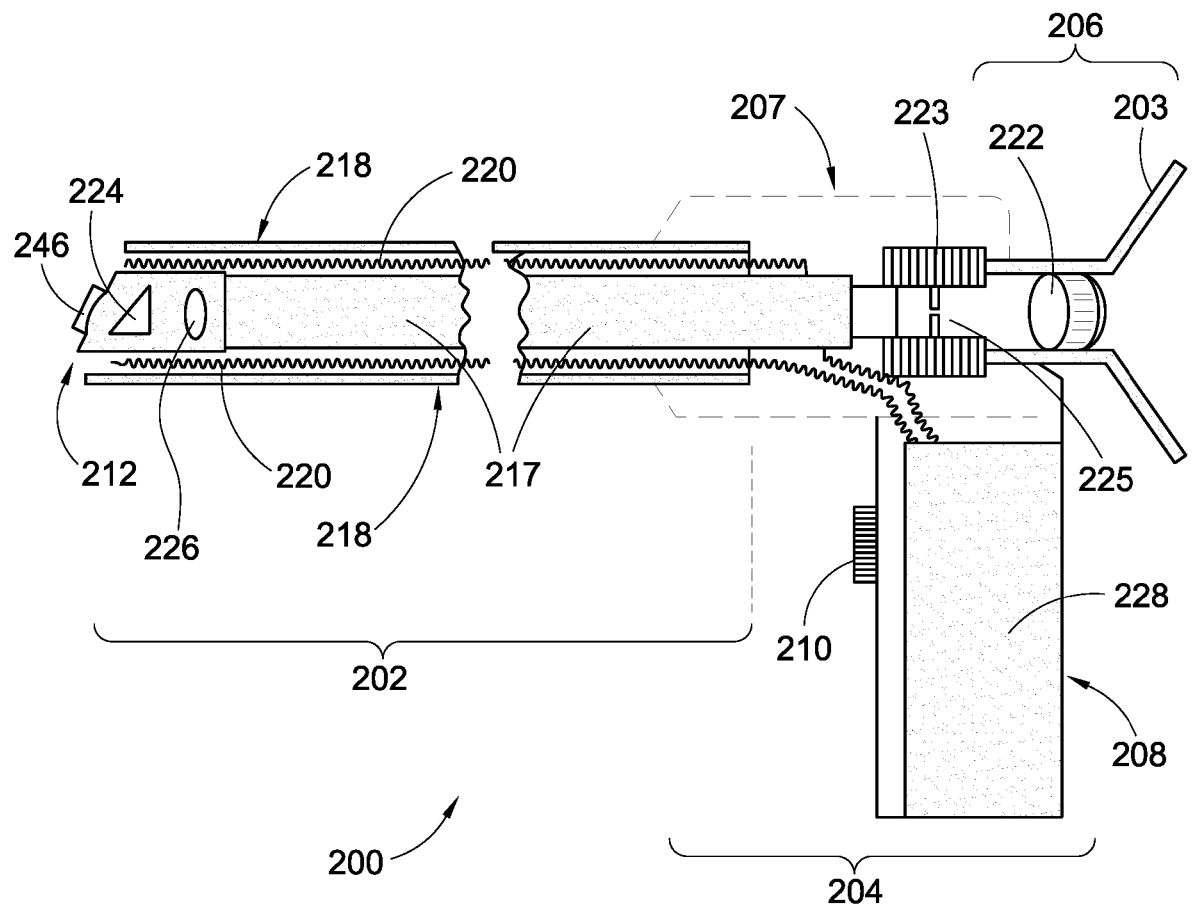
FIG. 2 is a schematic cross-sectional view of the endoscope illustrating a portion insertable into the patient's body or "insert" portion as well as a grip section of the endoscope. Also shown is an optical joint section joining the insert portion to the grip section and a view port for viewing an image of anatomical features inside the patient's body.

FIG. 2 is a simplified schematic diagram cross-section depicting the insert portion 202 and the handle portion 204 of an example endoscope 200. As discussed above, the handle portion 204 includes the optical joint section 207, the grip section 208 and the view port 206. The insert portion 202 comprises an elongated member 114 and a tip member 212 wherein the tip member 212 is positioned at the distal end of the elongated member 114. The tip member 212 houses optical components designed and arranged to capture light incident from an oblique direction with respect to optical path inside the insert portion. Hence, as illustrated, the tip has a front face that is angled obliquely with respect to the length of the insertable portion 202 and elongated member 114. These optical components may include, at least one front window or first lens 246, at least one redirecting optical element 224 (e.g., prism), and one rear or second lens 226. The redirecting element 224 can comprise prism or other a transparent element having reflective surfaces, that receives and reflects the incident light possibly via total internal reflection (TIR). In some examples, the redirecting element 224 also refract the light.) Alternatively, the redirecting optical element 224 may include reflective coatings (e.g. silver or dielectric coatings, etc.) that reflect light. The tip member 212 may also provide one or more seats or surfaces where one or more light emitting devices can be disposed. These seats may serve as thermal contacts for receiving heat from the light emitters. The elongated member 114 may include a lens tube 217, a conductive member (e.g., elongate conductive member) 220, for providing electrical power to the light emitter, and a protective tube 218, wherein the conductive member and the lens tube are housed inside the protective tube. The elongated member 114 has a distal end 211 and a proximal end 219. The distal end 211 (where the tip member is positioned) is inserted into a cavity of a body while the proximal end 219 is connected to the optical joint 207 and the viewport 206. The lens tube 217 is configured to support and align one or more lenses that convey the light captured by the tip member 212 toward the optical joint section 207 and the view port 206. The tip member 212 is connected to the lens tube 217, in certain designs, with a connection that facilitates ease of manufacture.

The insert portion 202, the lens tube 217, the conductive member 220 and the protective tube 218 can have length between 100 mm and 200 mm possibly between 120 mm and 180 mm or 140 mm and 160 mm or any range between any of these values or possibly outside these ranges. The optical joint section 207 can have a length between 50 mm and 150 mm in some implementations.

In some embodiments the tip member 212 and the lens tube 217 can be formed from materials with relatively high thermal conductivity (e.g., larger than 10 W/m.K) and sufficient stiffness to support the mechanical functionality of the endoscope. For example, the tip member 212 and the lens tube 217 may be made of copper or a copper alloy such as brass, or bronze, or may comprise stainless steel. In certain implementations, for example, the tip member 212 may comprise bronze or another copper alloy and the protective tube 218 comprises stainless steel. The lens tube 217 may also comprise stainless steel. The tip member 212 and lens tube 217 may thus provide a thermal conduction path that may dissipate the heat generated by the light emitters mounted on the tip member 212.

The conductive member 220, that may be disposed on the lens tube 217, provides electrical connection between the light emitter(s) (not shown) attached to the tip member 212, and a source of electrical power such as one or more batteries enclosed in the electronic compartment 228 positioned inside the grip section 208. A user interface 210 (e.g., one or more dials, switches, and/or buttons) may be provided on the grip section 208, to control the power transfer between the power source, e.g., the battery or batteries, and the light emitter(s). The conductive member 220 may comprise two or more wires or two or more conductive lines or strips embedded in one or more flexible membranes. The conductive lines may, for example, be imbedded in an insulating material with the conductive member 220 remaining a least somewhat flexible. In certain implementations, the flexible membranes can be formed to hold a shape, such as a curve shape, across a cross section perpendicular to the length of the conducive line. In certain implementations, the conductive member 220 comprises a ribbon cable. In other possible implementations, the conductive member 220 may be rigid. The light emitting devices, that are disposed on the tip member 212, can be connected to conductive member 220 possibly via two or more thin wires (for example soldered to the light emitter and the conductive member at two ends). Alternatively, the light emitting device may be at least partially embedded the same flexible and/or insulating membrane that contains the conductive paths, near the distal end of the conductive member. In such a case, the light emitting device and the conductive member 220 may be collectively referred to as a "light emitting conductive member". In some implementations, the light emitting device is partially embedded in insulating or flexible membrane that houses the conductive lines however a portion of the light emitting device is not covered by the insulating or flexible membrane and is instead exposed. In some implementations, the conductive member 220 having a light emitting device imbedded therein comprises a flexible (or flex) circuit.

In various implementations, the light emitting device comprises a solid state light emitter. In particular, the light emitting device may comprise a semiconductor light emitter such as a light emitting diode (LED). The light emitting device, for example, may comprise a semiconductor die with an LED fabricated thereon. The die can have a thick ness between 0.1 mm to 1 mm and an area between 1 millimeter squared and 10 millimeter squared. In some embodiments, the light emitting device may comprise an organic light-emitting diode (OLED). The OLED may comprise an organic material deposited on a solid die, or a soft layer. The die or the soft layer may have thickness between 0.05 to 1 mm and an area between 1 millimeter squared and 10 millimeter squared. LEDs and OLEDs, both can be a stand-alone device connected to the conductive member via wires, or completely or partially embedded in a flexible or semi-flexible membrane (forming a light emitting conductive member).

In some implementations, a diffuser may be disposed over the light emitting device to diffuse light emitted by the light emitting device. One or more LEDs for example may be outfitted with diffusers at the output thereof. In some implementations, for example, the surface of the light emitting device can be coated with an optically diffusive material to diffuse the light emitted by the light emitter. Alternatively, an optical diffuser may be mounted on the light emitting devices, which is mounted on the tip member 212. In some implementations, a plurality of light emitting devices are mounted on the tip member 212. In such cases, separate diffusers may be provided for different light emitting devices. However, in other implementations, one diffuser may be disposed in front of a plurality of light emitting devices. A diffuser may, for example, be disposed in front of two or three or possibly more light emitting devices. In some implementations, for example, an arcuate shaped (e.g., horseshoe or "U" shaped) diffuser may be disposed over two, three or possible more, light emitting devices such as LEDs. In some implementations, a ring-shaped diffuser may be disposed in front of a plurality of light emitting diffusers, e.g., LEDs, disposed about and entrance of the endoscope that is configured to receive the light reflected from the anatomical features into the endoscope. In some cases, a light guide may be used to diffuse or the light. Light from the light emitting device can be coupled into the light guide and coupled out to illuminate the target region. This light guide may be horseshoe or "U" shaped in some implementations. Diffused light may improve the uniformity of the illumination over the target region, resulting in better image quality.

In various implementations such as shown in FIG. 2, the protective tube 218 houses the lens tube 217, which contains the lenses therein. The tip member 212 is connected to the lens tube 217 and the conductive member 220 is disposed the lens tube and the tip member. As shown, the conductive member 220 is thus disposed between the lens tube 217 and the protective tube 218. The distal end of the protective tube (where the tip 212 is positioned) and junction between the protective tube and the optical joint 207, are sealed such that the conductive member and the lens tube 217 are completely isolated from the surrounding medium (e.g., body fluids, tissue, etc.). Optically transparent adhesives may be employed to provide such seals. In some examples, a sealing gasket or O-ring may be added between the protective tube 218 and the tip member 217 and/or between the protective tube 218 and the optical joint 207, in addition or instead of adhesives, to isolate the conductive member 220 and the lens tube 217.

The view port 206, that is connected to the support structure 223, may include an eye piece 222 and an eye cup 203 through which the user can observe the image of the target region. In certain designs, the eye piece 222 comprises two lenses although the eyepiece or ocular may comprise more or less lenses. In some implementations, the eyepiece comprise a lens with positive power and a lens with negative power, although other configurations are possible. One or both lenses may be spherical lenses although the design should not be so limited.

In various implementations, an eye cup 203 is included for comfortable placement of the eye for viewing an image of the target region formed with light passing through the endoscope. In some implementations, a virtual image is formed by the eyepiece, possibly at infinity or a large distance from the eyepiece. Accordingly, in some designs, the endoscope may be configured for viewing directly by peering into the endoscope with the eye. However, the endoscope can be configured for use with a camera. In some implementations, for example, the eye cup 203 may be replaced by camera including an optoelectronic image sensor on which the final image may be formed. In some implementations, a camera may be configured to mate with the eyecup so as to receive the image. In yet another implementation, the eyecup may be replaced by an opto-electronic image sensor that converts the image projected thereon to an electronic signal that may be provided to a display for viewing the image.

As discussed above, the optical joint section 207 facilitates connection of the lens tube 217 and alignment of the lenses therein with the eyepiece or ocular 222. In various implementations, therefore, the optical joint section 207 may include a support structure 223 (e.g., a cylindrical shell or tubular channel) that receives a portion of the last lens located at the distal end of the elongated member 214, and optically aligns it with the eyepiece 222. As illustrated in FIG. 2, an optical aperture 225 is included a distance from the last lens in the elongated member 214. This optical aperture may comprise a field stop and may be positioned at a location where an image is formed. This optical aperture 225 may be formed from black opaque plastic or metal. In various implementations this optical stop 225 has a circular opening for light to pass. The optical stop 225 is shown in FIG. 2 as positioned near the middle of support structure 223 although other variations are possible.

As discussed above, light is received by the tip member which includes a front window, a prism and possibly another lens. FIGS. 3A-3E show various perspective of the tip member.

FIG. 3A is an exploded view of the tip member showing various components included in the tip member 312 of the insert portion 102, 202. The tip member 312 comprises a housing 330 for supporting and aligning a plurality of optical components. Included in the housing is a first (front) lens 346 or window having optical power and an optical redirecting element 324 (e.g., a prism). FIG. 3A shows two inserts 344 that fit into two openings in the side of the housing. The openings are shaped to fit the prism therethrough, and the inserts are shaped to fit into the opening. An optical aperture 350 also included in the housing 330. A second (rear) lens 326 is also housed in the housing 330. The prism is shown disposed between the first and second (front and rear) lenses in this design. Also, in the example configuration shown, the optical aperture 350 is disposed in the optical path between the first and second lenses and, in particular, between the prism and the second lens. A spacer 348 is shown in FIG. 3A. This spacer 348 may be used to provide the appropriate spacing between the optics within the housing 330, e.g., the second (rear) lens 232 and the optics in the lens tube. In various implementations, the spacer 348 may also be configured to facilitate easy alignment and connection between the tip member 312 and the lens tube.

FIGS. 3B and 3C illustrate the front and back perspective view of the housing 330. In various implementations, the housing 330 is formed from a piece of a metal with high thermal conductivity such as copper or a copper alloy like bronze or brass or other alloy, although other materials may possibly be used. Bronze may be used as bronze provides both thermal conductivity and hardness that facilitates machining. The housing 330 comprises a front surface 332 that may include a front lens seat 334 and/or a light emitting device seat 335. The housing 330 shown also includes a left and a right side-wall 336 and an inner cavity 338. The housing may include a rear lens seat (not shown) and/or a rear spacer seat 342 for contact with the second (rear) lens and the spacer, respectively. In various implementations, the front and rear lens seats and the side-walls, may be shaped to provide a pathway through the inner cavity 338 of the housing that has a circular cross-section. In certain implementations, the openings in the side-walls 336, have a quadrilateral shape conforming to the shape of the redirecting optical element or prism 324. Likewise, in various implementations, the inner cavity 338 has a shape to fit the prism likely conformally on at least two sides of the prism such as the two sides of the prism that provide total internal reflection to direct light from the target region of the patient's body that is collected through the window onto the second lens and through the lens tube to form an image with the eyepiece.

As illustrated in FIGS. 3A-3E, the front surface 332 of the housing and the front lens seat 334 are tilted with respect at an oblique angle with respect to, for example, to the rear lens seat 340, the lens tube, the elongated member, etc. Likewise, the front (first) lens is tilted at the same or a similar oblique angle. The tilt angle may for example be between 20 and 40 degrees with respect to the rear (second) lens or rear lens seat.

In the design shown, the first lens or front lens 346 is also a window for the endoscope. This window/lens 346 has optical power, in the example shown, negative optical power that may potentially increase the field of view of the endoscope. In the design shown, outer surface of the lens 346 is flat and the inner surface is curved. In particular, in this case, the front lens 346 is a plano-concave lens with the curved surface comprising a concave surface resulting in a thickness that decreases from the edge toward the center. The curved surface is a spherical surface in this example. The front lens 346 may also be a bi-concave or convex-concave lens. The front lens 346 has a circular cross-section. Other types of lens with other types of surfaces, other shapes and optical parameters, are possible.

In the example shown, the refractive optical redirecting element 324 comprises a prism and in particular a quadrilateral prism. Other shapes are possible. The prism is disposed to receive light input through the front lens 346, which is tilted at an angle, and redirect the light more along the length of the lens tube and elongated member. In the design shown, the prism 324 includes at least two opposite surfaces that are configured to reflect light via total internal reflection to redirect the optical path from an oblique angle to a direction along the length of the elongated member 114 and lens tube 217. In the example shown, the prism includes a first surface through which light is input, a second and third surface which reflect the light within the prism and a fourth surface through which the light exits the prism so as to be directed down the lens tube.

In the design shown, the optical aperture 350 is disposed between the output surface of the prism and the second lens. The optical aperture 350 comprises a disc formed from an opaque material with an aperture such as a circular aperture therein.

In the example shown, the rear lens 326 has positive optical power and is a plano-convex lens. The lens 326 may also be bi-convex or have other designs. The rear lens 326 has a circular cross-section and comprises a flat surface and a spherical convex surface resulting in a thickness that increases from the edge toward the center. Other lenses with other shapes, however, may be used.

The front lens, the rear lenses, and the prism, may be formed from a dielectric material that is optically transparent at least within the 400 nm-1000 nm wavelength range. The said optical material may have a refractive index between 1.5 and 2. Each of the front lens, the rear lens, and the prism may comprise the same type of material, in some implementations, although the design need not limited to use of a single transparent optical material.

As shown, the housing 330 is shaped to receive the first lens 346, the prism 324 and the second lens 326. In the example shown, at least one opening 338 in the sidewalls 336 of the housing or both openings have a profile that is similar to that of the prism such that prism fits therethrough. Portions of the cavity inside the housing may also have surfaces that match the profile of the prism to support, position, and alignment of the prism. The two inserts 344 can be formed from the same material used to form the housing 330. These inserts 344 may have a profile similar to those of the prisms and the openings 338. The shape and curvature of the inserts 344 may conform to the shape of the openings provided on the side-walls 336 of the housing 330. Other designs, however, are possible. For example, only one opening and insert may be included and the insert or inserts may be excluded in certain designs.

The spacer 348 is a hollow cylinder with, in this design, has a uniform inner diameter and an outer diameters that is different for distal and proximal portions. In the design shown, the outer diameters of the two portions changes from the first diameter for the distal portion to the second diameter for the proximal portion. In the example shown this transition occurs near halfway along the length of the cylinder although other designs are possible. The transition between the first and second diameters, which in this case is abrupt, forms on one side, an edge which abuts the proximal end of the housing. The proximal edge of the spacer 348 may in some cases abuts the next lens (the third lens) which may comprise a rod lens. The length of the spacer 348 therefore can establish a proper distance between the second and third lenses. The spacer 348 may be comprise a material similar to the one used to form the housing 330. The spacer 348 may, for example, comprise a copper alloy such as bronze or brass, although other materials may be employed.

Figure 3D:
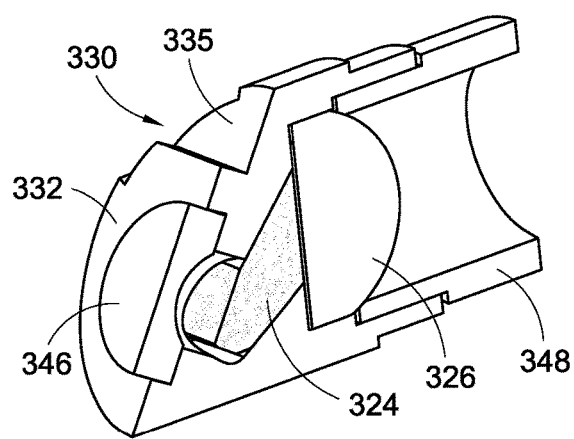
FIG. 3D illustrates three-dimensional cross-sectional of the assembled tip member.
Figure 3E:
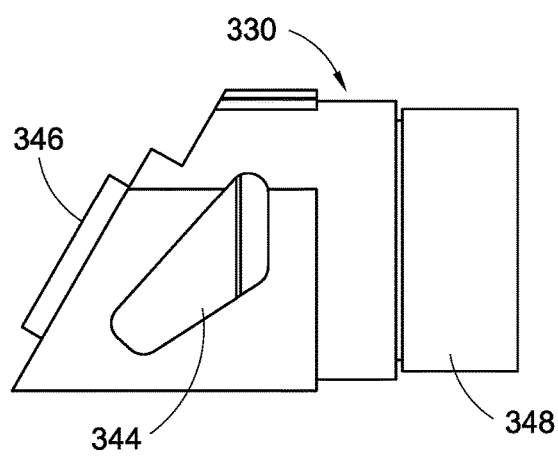
FIG. 3E illustrates the side-view of the assembled tip member.

FIGS. 3D and 3E show three-dimensional (3D) cross-sectional and side views of the assembled tip member 312 where the constituents of tip member 312 are added to the housing 330. The front lens 346 is positioned in the front lens seat 334. Accordingly, the front lens seat 334 has a size, e.g., diameter, that fits the diameter of the front lens 346 so as to position and align the front lens. In the design shown in FIGS. 3D, the housing 330 of the tip member 312 has a rear lens seat 340 formed by an opening having a first inner diameter that fits the diameter of the second lens so as to position and align the front lens. This opening in the housing also as a second inner diameter more proximal that the first inner diameter. This second inner diameter is larger than the first inner diameter. The second larger diameter is configured to form a spacer seat for receiving the spacer 348. The second diameter fits the outer diameter of the first distal portion of the spacer 348 so as to position and align the spacer in this opening of the housing. This configuration provides for increased ease of manufacturing as the second lens can be inserted into the housing fitting into and supported within the rear lens seat 340 and the spacer 348 can be inserted into this same housing fitting into and supported within the spacer seat. As illustrated, the optical aperture 350 is also positioned inside the rear lens seat 340 such that the optical aperture is disposed between the rear lens 326 and the prism 324. The spacer 348, which is placed inside the spacer seat 342, aligns and stabilizes the rear lens 326.

As illustrated, the prism 324 is positioned inside the inner cavity 338. The inserts 344 are inserted into the openings 338 provided on the side-walls 336. These housing and possibly the inserts may optically align the prism 324 with respect to the front lens 346 and rear lens 326. The inserts may also be useful in isolating the inner cavity 338.

One or more solid-state light emitters (not shown) may be attached to the light emitting device seat 335, for example, using a thermally conductive glue. The one or more light emitting devices may comprise one or more stand-alone devices; for example a single emitter on a single die, multiple emitters on a single die or multiple emitters on multiple dies. Alternatively, the light emitting devices may be integrated with a conductive cable such as the flexible conductive member 220 discussed above. For example, the light emitting device may be embedded inside one end of the flexible (e.g., plastic) membrane where one or more conductive lines or strips are also embedded. In the latter case, the light emitting end of the light emitting conductive membrane may possibly be glued to the light emitting device seat 335.

The components included in the tip member 312 may be configured to illuminate a target region and capture the reflected light (by the target region) incident from an oblique direction relative to the optical axis of the rear lens 326, the optical axis of one or more lenses in the lens tube 217, the length of the lens tube 217, the length of the elongated member 114, or any combination thereof. The light emitting devices generate light that is directed on the target and may contain a narrow or broad range of wavelengths. All or a subset of these wavelengths maybe reflected by the target region toward the front lens 346. The front lens 346, the prism 324, and the rear lens 326 collect light reflected from the target region and alter the angular distribution of the light rays incident on the front lens 326 redirecting them toward the subsequent optical elements (e.g., the rod lenses inside the lens tube 217). In various implementations, this light contributes to the formation of a real image of the target region at the proximal end of the lens tube. In certain optical designs, the aperture 350 servers as an aperture stop that limits the light rays incident on the rear lens 326. In some designs, elimination of certain light rays from contributing to image formation may reduce certain aberrations and improve the quality the final image formed by the subsequent optical elements. As discussed above, the negative power of the front lens or window 346 may increase the field of the view of the scope by allowing light rays incident with a broader range of incident angles to contribute in the image formation.

In some designs, the optical elements included in the tip member 312, effectively serve as an objective lens that provides an image to the optical components inside the lens tube, which relay that image to a real image, for example, formed inside optical joint section 207 or a virtual image to be viewed, e.g., by the user's eye. One or more intermediate images may be formed before the final image. In some implementations, the optical imaging system is designed such that the combination of the lenses included in the tip member 212 and lenses in the lens tube 217, collectively generate a high quality image of the target region (located near the tip member 212) at the opposite end of the lens tube (e.g., inside the optical joint section).

Figure 4A:
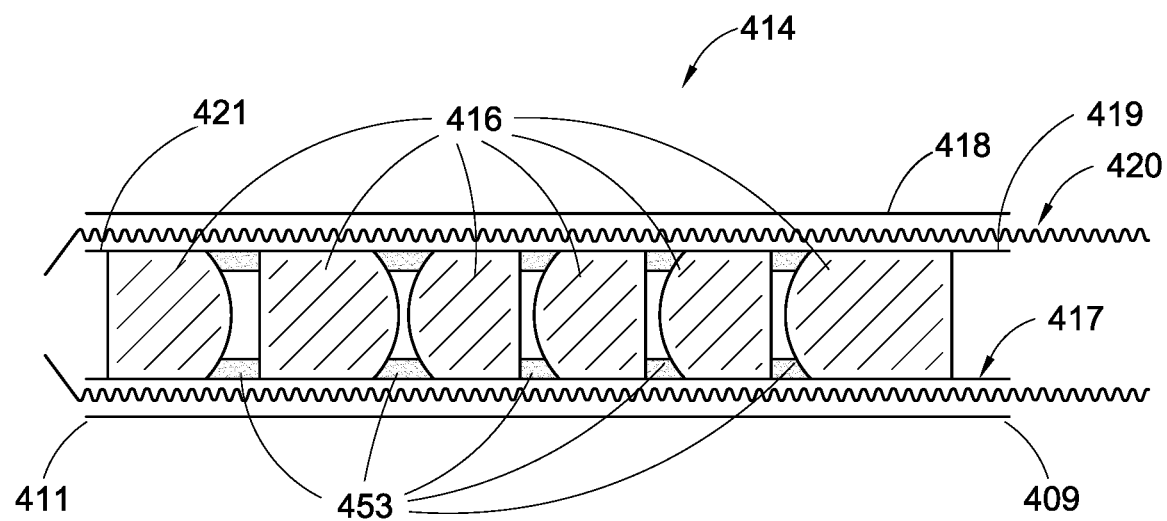
FIG. 4A is a schematic cross-sectional view of the elongated member of an example endoscope design.

FIG. 4A is a schematic diagram illustrating a simplified cross-sectional view of the elongated member 414 according to some embodiments of the disclosed endoscope. The elongated member 414 has a distal end 411 and a proximal end 409, and comprises: a protective tube 418, a lens tube 417 having a distal end 421 and a proximal end 419 within the protective tube, a plurality of rod lenses 416 with the lens tube and a conductive member (e.g., elongate conductive member) 420. In this design, the conductive member is disposed between the lens tube 417 and the protective tube 418. The lens tube 417 supports and laterally aligns the lenses such as rods lenses 416 with respect to each other. The inner diameter of the lens tube 417 may be equal to the diameter of the rod lenses to provide reduce lateral misalignment between lenses, for example, after the lenses are inserted into the lens tube. The longitudinal spacing between each pair of rod lenses, can be precisely established and stabilized using the spacers 453 such as O-ring spacers placed between each rod lenses. The O-ring spacers 453 may be formed from dielectric or metallic material with sufficient stiffness and to maintain a given distance between adjacent lenses over extended period of time and possibly under mechanical stress. In some designs, the spacers 453 may comprise the same material used for forming the tip member 412 such as a copper alloy like bronze or brass. Other materials, may be used however. In some designs, for example, the spacers 453 may comprise the same material used for forming lens tube 418, such as stainless steel. The O-ring spacers 453 may have an inner diameter close to the outer diameter resulting in which case they may be considered cylindrical shells. A large inner diameter may increase the throughput of light by not decreasing the effective aperture of the rod lenses while maintaining the inter-lens spacing. In various designs, the outer diameter of the spacer may be equal to the inner diameter of the lens tube 417 such that the spacer fits within the lens tube.

Figure 4B:
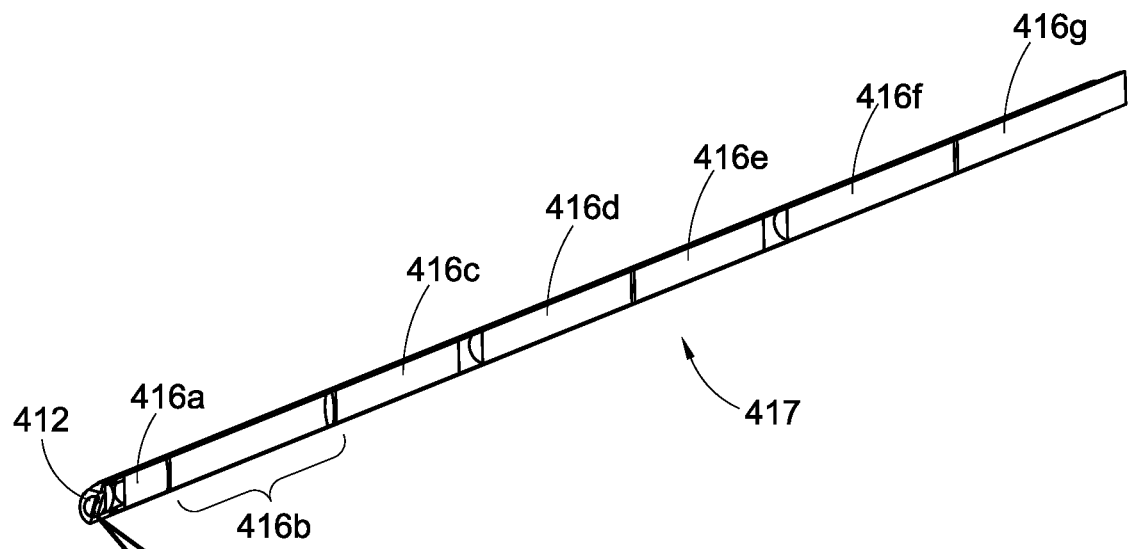
FIG. 4B illustrates a cutaway perspective view of the assembled insert portion of an endoscope showing optical elements within a lens tube housed within a protective tube.
Figure 4C:
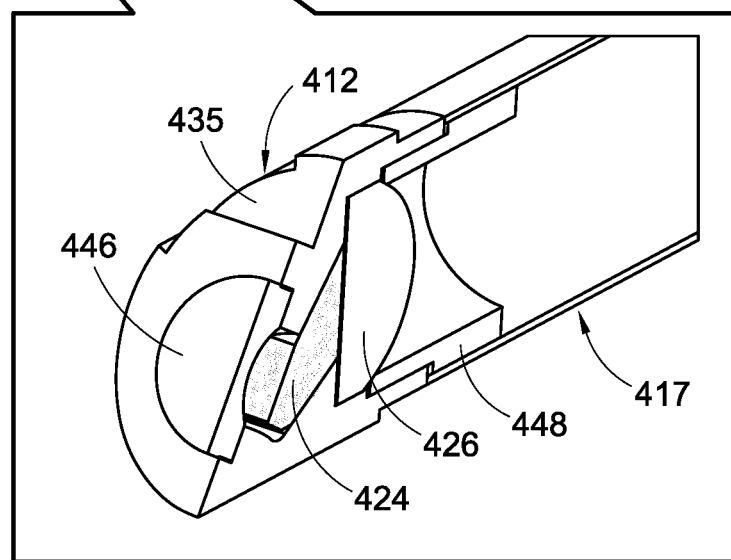
FIG. 4C is a close-up view of the distal end of the insert portion (without a protective tube) that shows the junction between the tip member and the lens tube.

FIG. 4B illustrates a cutaway perspective view of the assembled insert portion 402 of the endoscope 100 (comprising a tip member 412 and an elongated member 414). FIG. 4C illustrates a close-up cross-sectional view of the junction between the tip member 412 and the lens tube 417. As discussed above, the spacer 448 serves as a mechanical link between the tip member 412 and the lens tube 417. In various designs such as shown in FIG. 4C, for example, the first outer (distal) diameter of the spacer 448 is equal to the inner diameter of the spacer seat 342 and the second outer (proximal) diameter of the spacer 448 is equal to the inner diameter of the lens tube 417 such that a portion of the spacer 448 may fit into the housing and a portion of the spacer 448 may fit into the lens tube. As mentioned above, The spacer 448 may also set the distance between the rear lens 426 and the first lens 416*a* in the lens tube while mechanically stabilizing them as the distal end of the spacer may be located and possibly contact the second lens while the proximal end of the spacer may be located at and possibly contact the third lens (e.g., the first or most distal lens in the lens tube). This arrangement results in a robust optical alignment between (e.g., the optical axis of) the rear lens 426 of the tip member and the (e.g., optical axis of the) first rod lens (which may be is aligned to subsequent rod lenses in the lens tube 417 and/or the optical axes thereof). Such lateral optical alignment may be achieved upon connecting the tip member 412 to the lens tube 417 by inserting the spacer 448 into the tip member and the lens tube into the spacer resulting in a simplified and low cost fabrication procedure. Given that the tip member 412 and the lens tube 417 may be made of thermally conductive materials (e.g., copper, brass, bronze, etc.), in some implementations, the junction between the tip member 412 and the lens tube 417, can be a thermally conductive junction. As such, the heat generated by the one or more light emitting devices attached to the light emitter seat 435, may be dissipated through the said junction.

The first lens positioned at the distal end 421 of the lens tube 417 receives the light exiting the rear lens 426 of the tip member 412. Subsequently the light pass through the sequence of the lenses and a rod 416*a*-416*g* in the lens tube 417. In various implementations one or more of the lenses in the lenses tube comprise rod lenses. In some implementations a rod (with no optical power) may also be included in the sequence. In certain implementations, most lenses within the lens tube (e.g., greater than 50% of the lenses) comprise rod lenses. In some implementations, the percentage of lenses in the lens tube that comprise rod lenses is more at least 60%, 70%, 80%, 90%, 95% or 100% or any range formed by any of these values. In the design illustrated, each of the lenses in the lens tube comprise rod lenses. The rod lenses have a length to width or diameter ratio of at least 2 possible at least 3, 4, 5, or more or any range formed by any of these values. Using rod lenses within the lens tube 417 may increase the ease of manufacture as the rod lenses may be more stable when set down to be fed into the lens tube and/or may be more stable within the lens tube. In the example shown in FIG. 4C, the first rod lens 416*a* has a shorter length than the other rod lenses 416*b*-416*g*, however, other arrangements and lengths are possible for the lenses.

In certain designs, the light from the target region that propagates through the plurality of lenses and a rod 416*a*-416*g* within the lens tube 417 forms a final image in the vicinity of the proximal end 419 of the lens tube. This image may be projected into the user's eye by the eyepiece 222 or captured by a camera having an image sensor therein. The last lens 416*g*, in the sequence of lens 416*a*-416*g* in the lens tube 417, partially extends outside of the lens tube. In various designs, the exposed portion of the last lens 416*g* may be received by the support structure 223 inside the optical joint section 207. The support structure 223 in this example thus has an opening with an inner diameter that fits the width or diameter of the last lens 416*g* in the lens tube.

In one design shown in FIG. 4B, the number of a lens and the number of rod lenses in the included inside the lens tube 417 is seven (7). This number may be larger or smaller in other designs. In certain implementations, however, the number of lenses in the endoscope is 12 or less, 11 or less, 10 or less, or 9 or less or any range between any of these values, for example between 9-12 or 9-11 etc. The number of lenses may possibly be less, for example 8, in some designs. Likewise, the number of lenses in the lens tube may be 10 or less, 9 or less, 8 or less, or 7 or less or any range between any of these values, for example between 7-10 or 7-9 etc. The number of lenses in the lens tube 417 may possibly be less, for example 6, in some designs.

In the example shown in FIG. 4B, of the lenses included in the lens tube (as well as of the lenses included in the endoscope) two of the lenses are combined (e.g. cemented together) to form a doublet 416*b* while the others are singlets. The doublet may comprise lenses having two different materials and may be designed to provide chromatic correction. In the design shown, the first (most distal) lens 416*a* in the lens tube (and the first or most distal rod lens) may be a singlet lens. In the example shown, this first lens 416*a* comprises a rod lens that is shorter than the other rod lenses. In this example, this first lens 416*a* comprises a positive lens, and may be a plano-convex or bi-convex rod lens although other shapes and types are possible. The second lens (second most distal lens) in the lens tube (and the second rod lens) is combined with the third lens (third most distal lens) in the lens tube 417 (and the third lens) to form a doublet 416*b*. This doublet 416*b* may comprise, for example, a negative and a positive lens cemented together. The doublet 416*b* may comprise, for example, a plano-concave, concave-convex, bi-concave rod lens glued to a bi-convex or plano-convex or concave-convex lens. In this example, this doublet 416*b* includes an aspheric surface. This aspheric surface may provide aberration correction. The component 416*c* following the doublet 416*b*, may be a rod with no optical power (flat entrance and exit surfaces), the fourth lens 416*d* (the fourth most distal lens in the lens tube) may be a positive powered lens such as plano-convex, bi-convex or concave-convex rod lens. Similarly, the fifth 416*e*, sixth 416*f* and seventh 416*g* lenses (fifth, sixth and seventh most distal lenses in the lens tube) may be positive lenses such as plano-convex, bi-convex or concave-convex rod lenses. As shown, the fourth 416*d*, fifth 416*e*, sixth 416*f* and seventh 416*g* lenses, comprise rod lenses. In this example, the sixth 416*f* and seventh 416*g* lenses (the two most proximal lenses in the tube) are identical. Using the same lenses may reduce inventory and simplify manufacture. Note that as discussed above, the endoscope includes optical elements including powered optical elements in the tip member. Accordingly, the first distal most lens 416*a* in the lens tube 417 corresponds to the third distal most lens in the endoscope. Similarly, the most proximal lens in the lens tube 417 corresponds to the seventh lens 416*g* in the lens tube and the ninth lens in the endoscope. Other of the lenses in the lens tube 416*b*, 416d, 416*e*, 416*f* (from distal to proximal), correspond to the fourth and fifth (forming a doublet), sixth, seventh, eighth lenses in the endoscope.

In various implementations, the optical elements included in the tip member 412 and the lens tube 417, may be formed from optical materials with refractive indices in the 1.6-2 range and Abbe numbers in the 20-70 range. The single or singlet lenses (and possibly the prism) may comprise the same material and therefore may have the same refractive indices while the two lenses forming the doublet may have a refractive index different from each other and potentially different from that of the singlets. In various implementations, the rod lenses may have the same diameters although the lengths may vary between various of the rod lenses. In certain designs, most of the aberration corrections (e.g., monochromatic aberration) may be distributed among the multiple lenses components; in these designs, the total number of rod lenses and the optical power of each lens may be less compared to cases where the aberrations are corrected in individual lenses. However, in other designs, aberration correction as well as other possibly individually lenses may have specific functions such as being objective lenses, field lenses and/or relay lenses. In other designs, the optical functions of the lenses are not as distinct. In various designed, the curvature of the surfaces of the lens is increased to reduce aberration.

Although a specific example of an arrangement of specifically shaped lenses having certain optical parameters (such as index of refraction and optical power) are shown, the selection and arrangement of lenses can be different.

As discussed above, the conductive member 420, that may be disposed on the lens tube 417 may provide one or more electrically conductive paths from the distal end 411 to the proximal end 409 of the elongated member 414. This conductive path may be used to transfer electric power, for example, from one or more batteries enclosed in the electronic compartment 228 to the light emitting device(s) connected to the tip member 412. The conductive member 420 may, however, have a variety of different configurations and/or possible form factors. For example, the conductive member 420 may comprise one or more pair of conductive lines extending from the proximal end 409 to the distal end 411 of the elongated member 414. These lines may be embedded in an insulating membrane. This insulating membrane may comprise a flexible membrane and may comprise for example plastic, polyimide, PEEK. The flexible membrane, may be able to flex or bend along its length or width. In some implementations, the flexible membrane may hold a preformed shape. The flexible membrane may, for example, be curved in the lateral direction (e.g., have a curved cross-section) and maintain that curvature. In some examples, when the flexible membrane (conductive member 420) is bent or flexed along its length or width, it may maintain its curved cross-section when the bending or flexing force is removed.

In some implementations, the conductive member 420 is longer than wide by 2, 3, 4, 5, 6, 8, 10, 15, 20 or more times or may have a length to width ratio in any range between any of these values. The conductive member 420 may, however, have a thickness much smaller than its width or length. This reduced thickness may provide for increased flexibility.

Figure 4D:
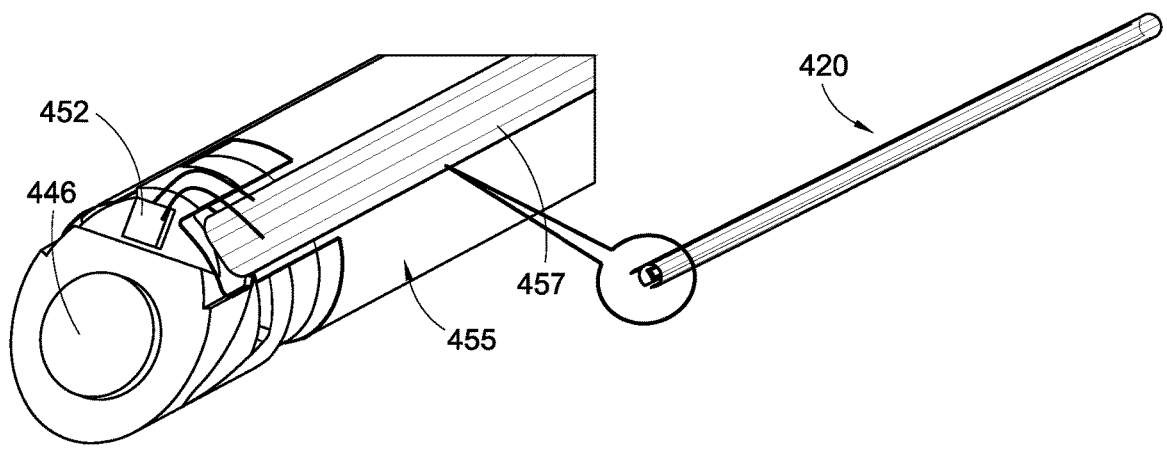
FIG. 4D is a perspective view of a flexible conductive membrane (right) and the distal and the end of the insert member (without a protective tube) showing the flexible conductive membrane disposed on the tip member and the lens tube to transport electrical power to a light emitting devices such as an LED. The flexible conductive membrane comprises conductive strips embedded in a flexible insulating membrane. In this example design, the conductive strips are connected to the light emitter via wires.
Figure 4E:
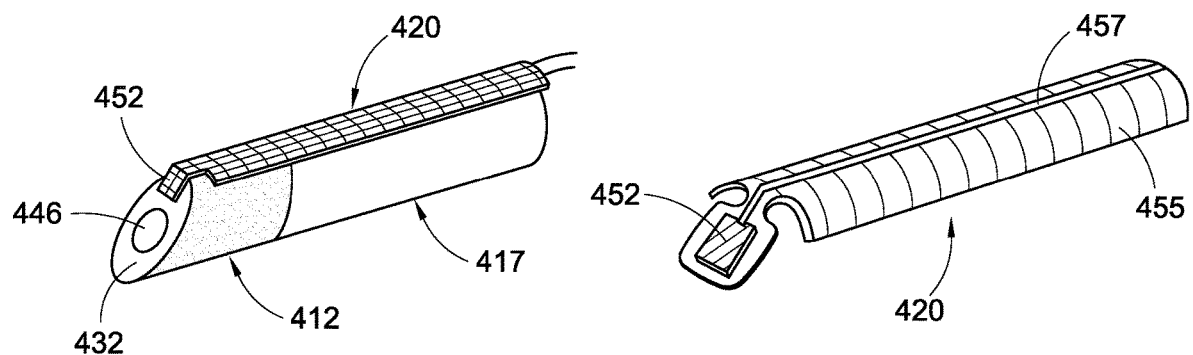
FIG. 4E illustrates a light emitting conductive member comprising a flexible conductive member (e.g., a flex circuit) that includes a light emitting device such as an LED.

At the distal end 411 of the elongated member, these conductive lines may be connected to the light emitting devices (that are attached to the tip member), for example, by soldering the conducting lines directly to the light emitting device or via wire bonds or connections. FIG. 4D shows an example a conductive member 420 comprise of plurality of elongated conductive lines or strips 457 embedded inside one or more elongated flexible membranes 455 formed from a soft or semi-rigid dielectric material (e.g., polyimide, thermoplastics such as PEEK). The conductive lines or strips 457 may provide electrical connectivity between the two ends of the elongated flexible membrane 455. The membrane 455 may be preformed with an arcuate shape such that the flexible membrane 455 can be conformably wrapped or fit around a portion of (e.g., the circumference of) the lens tube 417. In another design (shown in FIG. 4E), the conductive member 420 may comprises a "light emitting conductive member" or a "flexible circuit" (also called "flex circuit"), wherein the flexible membrane 455 that includes elongated conductive lines or strips 457, also emits light from one end. In this case, a light emitting device 452 (e.g., an LED) may be embedded in one end (e.g., the distal end) of the flexible membrane and be internally connected to the conductive liens or strips 457 (that are also embedded in the flexible membrane). The light emitting device 452 may have a portion thereof that is covered by the insulating material and may have a portion that is not covered and is exposed or the light emitting device 452 may be entirely covered by the dielectric material. The light emitting conductive member 420 may also be preformed with an arcuate shape, for example, such that it can be conformably wrapped or fit around a portion of (e.g., the circumference of) the lens tube. The light emitting conductive member 420 may comprise a flexible membrane that can be flexed along its length or width and maintain it cross-sectional shape (e.g., a curved shape) when the flexing force is removed.

Figure 4F:
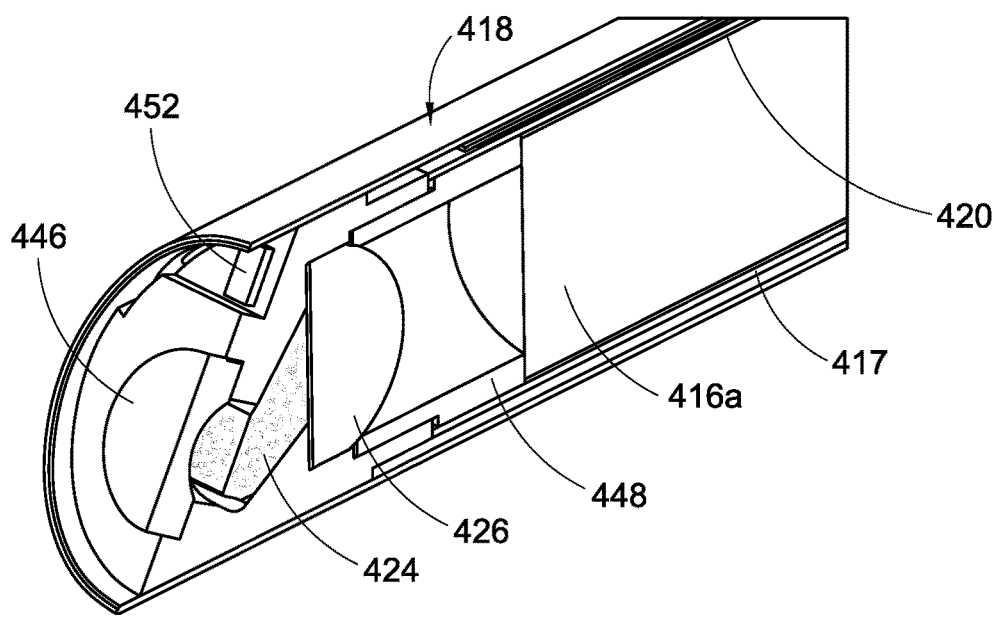
FIG. 4F is three-dimensional cutaway view of the distal end of the fully assembled insert portion.

FIG. 4F illustrates three-dimensional view of the distal end 411 of the assembled insert portion 202 comprising the distal end 411 of the elongated member 414 connected to the tip member 412. As illustrated, the protective tube 418 fits over the outer diameter of the proximal portion of the spacer 348. Accordingly, the protective tube 418 may have an inner diameter that is the same as the outer diameter of the proximal portion of the spacer 348. This protective tube 418 then may abut or come close to the end of the housing 330 of the tip member 312. Such a configuration increases the ease of fabrication as the proximal end of the spacer 348 may be inserted into the distal end of the lens tube 417 and the protective tube may be slipped over the lens tube and the proximal end of the spacer to provide alignment of the optics within the tip member and the lens tube. In some implementations such as shown, the outer diameter of the protective tube 218 has a size, e.g., diameter that is the same as that of the housing 330 of the tip member 312. As mentioned above, adhesive may be provided at the connection between the protective tube 418 and the tip member 412.

Figure 4G:
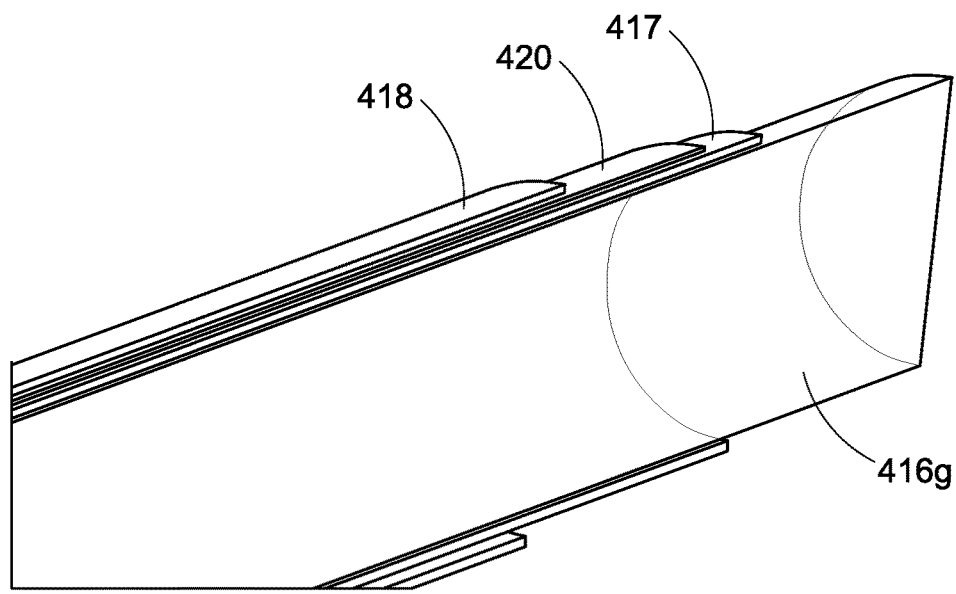
FIG. 4G is a three-dimensional cross-sectional view of the proximal end of the fully assembled insert portion showing the lens tube having the conductive member thereon both housed within the protective tube.
Figure 4H:
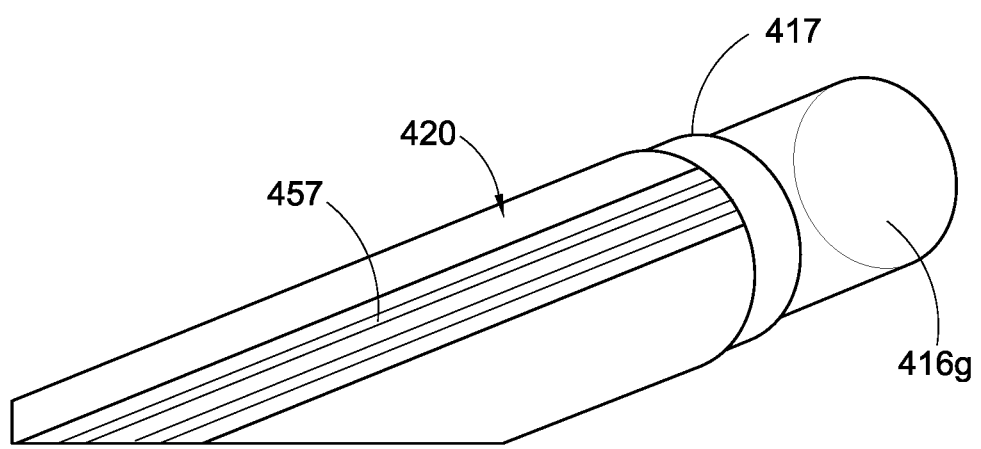
FIG. 4H is a three-dimensional view of the proximal end of the lens tube and the conductive member disposed thereon.

FIG. 4G is the 3D cross-sectional view of the proximal end 409 of the assembled insert portion 402 showing the lens tube 417, conductive member 420 and the protective tube 418. FIG. 4H is the 3D perspective view of the proximal end 419 of the lens tube 417 and the conductive member 420 disposed thereon. As illustrated, in this example, the most proximal lens 416*g* in the lens tube 417 extends beyond the lens tube and the protective tube 418.

The protective tube 418 houses both the lens tube 417 and the conductive member 420 disposed thereon. The protective tube may be formed from a material that does not chemically interact with the body fluids and/or tissues in which it may be inserted to. For example the protective tube can be formed from stainless steel or copper alloys.

Figure 5A:
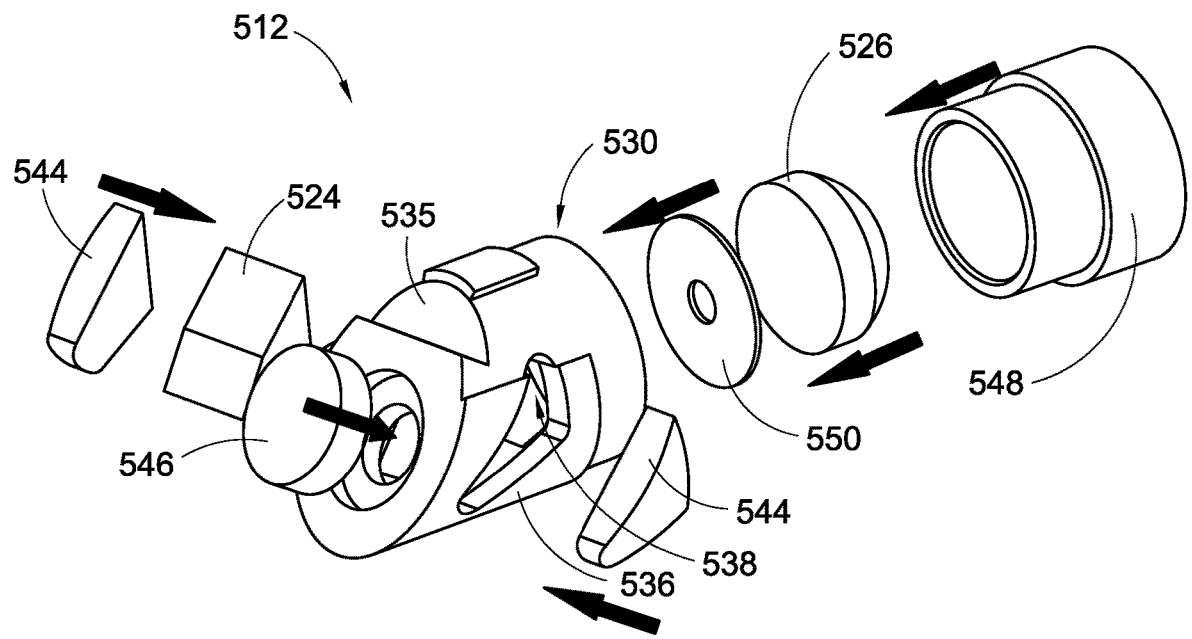
FIG. 5A illustrates an example method that may be used to assemble the tip member. Components are inserted into cavities within the housing of the tip member through openings provided on the housing. Some components may be mounted against seats on the housing.

FIG. 5A Illustrates an example of the method that may be used to assemble the tip member 512. First a housing 530 is provided; next all the components are inserted into seats, cavities and openings provided on the housing 530. The window 546 is inserted into the window seat 534. The prism 524 is inserted to the internal cavity 538 via one of the opening provided on one of the side-walls 536. One or two centering inserts 544 are inserted into one or two of the openings provided on the side-walls 536. In some cases, these inserts may optically align the prism 524 with respect to the front lens 546 and rear lens 526 and stabilize its positioning through the lifetime of the device. The optical aperture 550 may be inserted into the lens seat (not shown). The rear lens 526 is also inserted into the lens seat and pushed against the optical aperture 550. The spacer 548 is inserted into the spacer seat (not shown) and pushed against rear lens 526. The spacer 548 stabilizes the position of the rear lens 526. One or more light emitters 552 are disposed and glued on the emitter seat 535 possibly using a thermally conductive glue. If instead of one or more separate light emitting devices (e.g., provided as separate semiconductor dies), a light emitting conducting member (e.g., flex circuit) is used, the light emitting end of the light emitting conductive member may be glued to the emitter seat 535 with the light emitter located on the emitter seat.

Figure 5B:
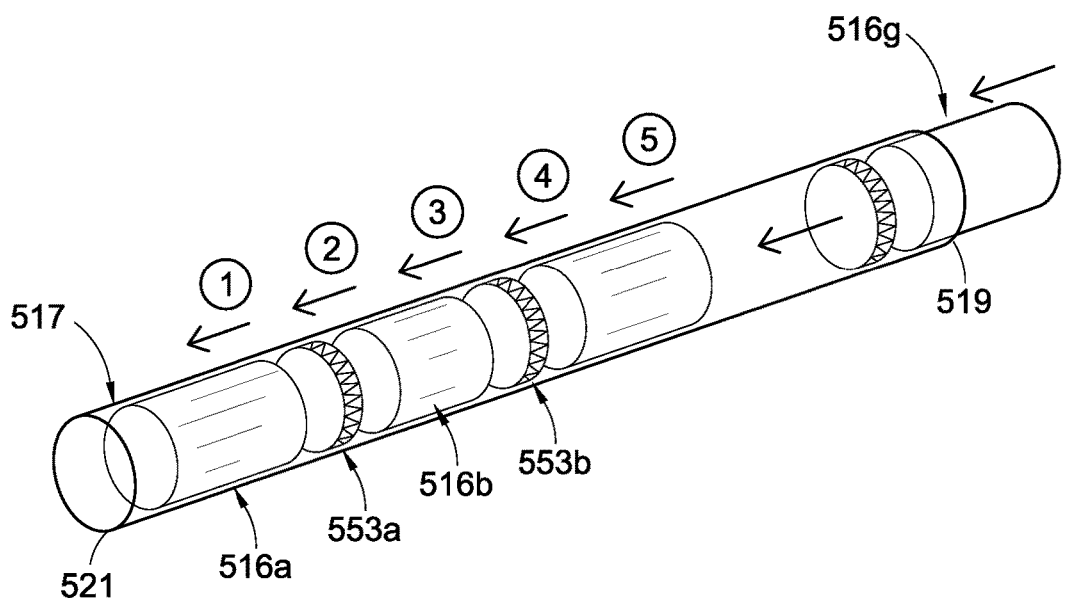
FIG. 5B illustrates an example method of assembling the elongated member. The rod lenses are sequentially inserted into the lens tube.
Figure 5C:
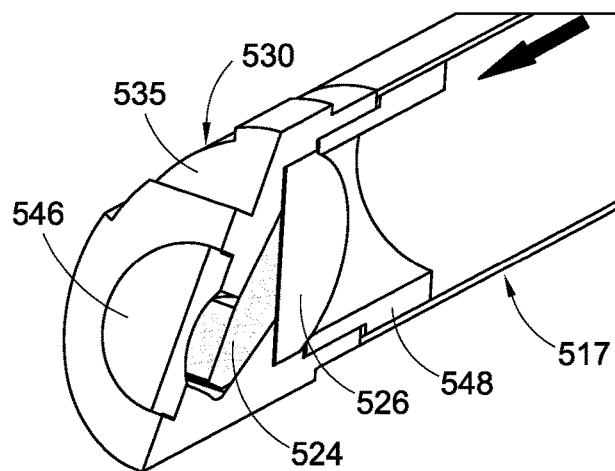
FIG. 5C is a cross-sectional view of the tip member attached to the distal end of the elongated member.
Figure 5D:
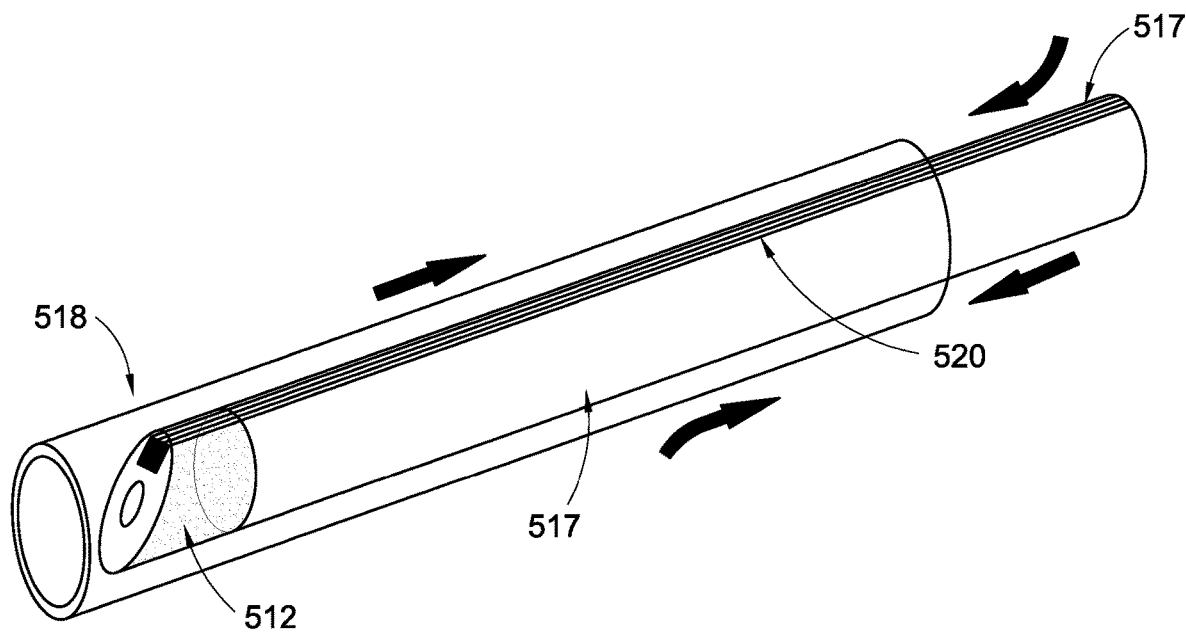
FIG. 5D illustrates a step of assembling the insert portion wherein the lens tube, together with the tip member and the conductive member (e.g., elongate conductive member) disposed thereon, are inserted into the protective tube.

FIG. 5B-5D illustrate an example of the method that may be used to assemble the elongated member 414. First, a lens tube 517 is provided (FIG. 5B). Next the first rod lens 516a is inserted into the lens tube 517 followed by the first O-ring spacer 553a. Next the second rod lens 516b is inserted into the lens tube 517 followed by the second O-ring spacer 553b. More lens rods and spacers are inserted sequentially. The length of the lens tube 517 may be selected such that a portion of the last rod lens 516g remains outside of the lens tune 517. In some designs, this portion of the last rod lens 516g may be inserted into the support structure 223 provided inside the optical joint section 107 possibly to provide optical alignment and/or positioning.

Next, tip member 512 may be attached to the lens tube 517 by inserting the rear section of the spacer 548 into the lens tube 517. FIG. 5C illustrates the cross-sectional view of the tip member 512 attached to the distal end 421 of the lens tube 517. Next, The conductive member (e.g., elongate conductive member) 520 may be disposed and attached to the outer region of the lens tube 517 such that its conductive elements (e.g., wires or strips) at one end are positioned near the light emitting device(s) 552 (mounted on the tip member 512). The conductive elements are then electrically connected to the light emitter device(s) 552. Alternatively, if a light emitting conductive member 520 is used, its light emitting end having the light emitter thereon may be glued to the light emitting seat 535 provided on the tip member 512. Then the rest of elongated portion of the light emitting conductive member is attached to the lens tube 517. FIG. 5D illustrates the final step of assembling the insert portion. The lens tube 517 together with the tip member 512 and the conductive member 520 attached to it, are inserted into the protective tube 518. As mentioned earlier, an optically transparent adhesive may be used to seal the gap that may exist between the tip member 512 and the protective 518. The cross-sectional perspective view of the distal end of the assembled insert section is shown in FIG. 4F. Although an example method of assembly has been discussed above, the insert portion and the endoscope may be assembled using different methods. For example, one or more additional steps may be added and/or one or more additional steps may be removed. Additionally, the order of the steps may be varied.

Figure 6:
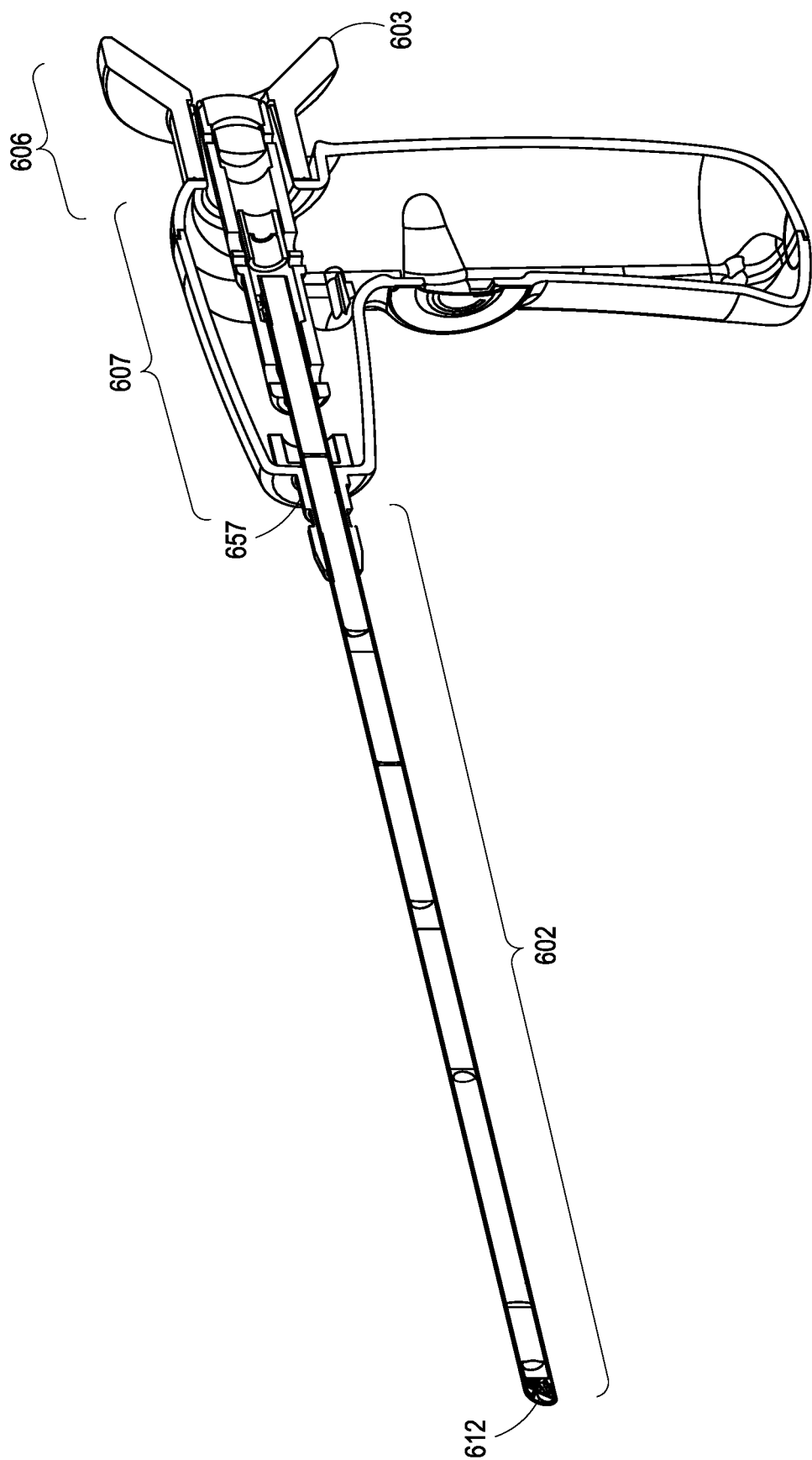
FIG. 6 illustrates a cross-sectional view of the fully assembled endoscope. The proximal end of the insert portion is connected to the optical joint section resulting in a complete optical path from the tip member to the view port.

FIG. 6 shows the cross-sectional view of the fully assembled endoscope. The proximal end 409 of the assembled insert portion 602 may be inserted to the optical joint section 607 through the opening 657 provided on the optical joint section 607 resulting in a complete optical path extending from the window on the tip member 612 to the view port 606, where the image can be viewed through the eyecup 603.

Figure 7A:
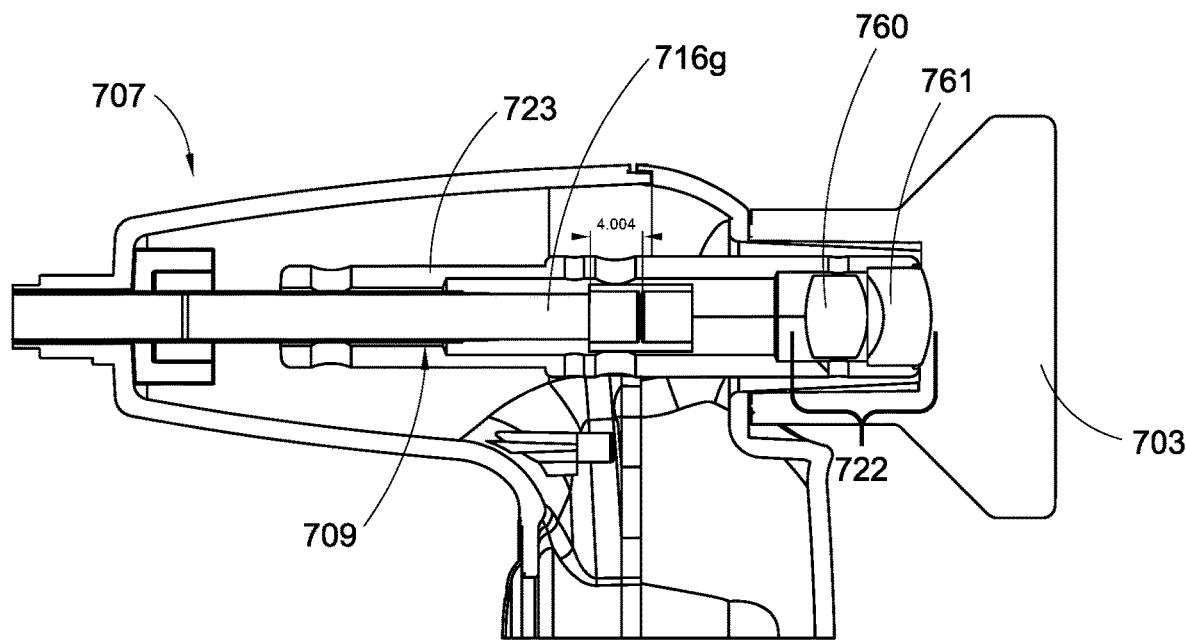
FIG. 7A illustrates a close-up cross-sectional view of the optical joint section of the example endoscope shown in FIG. 6
Figure 7B:
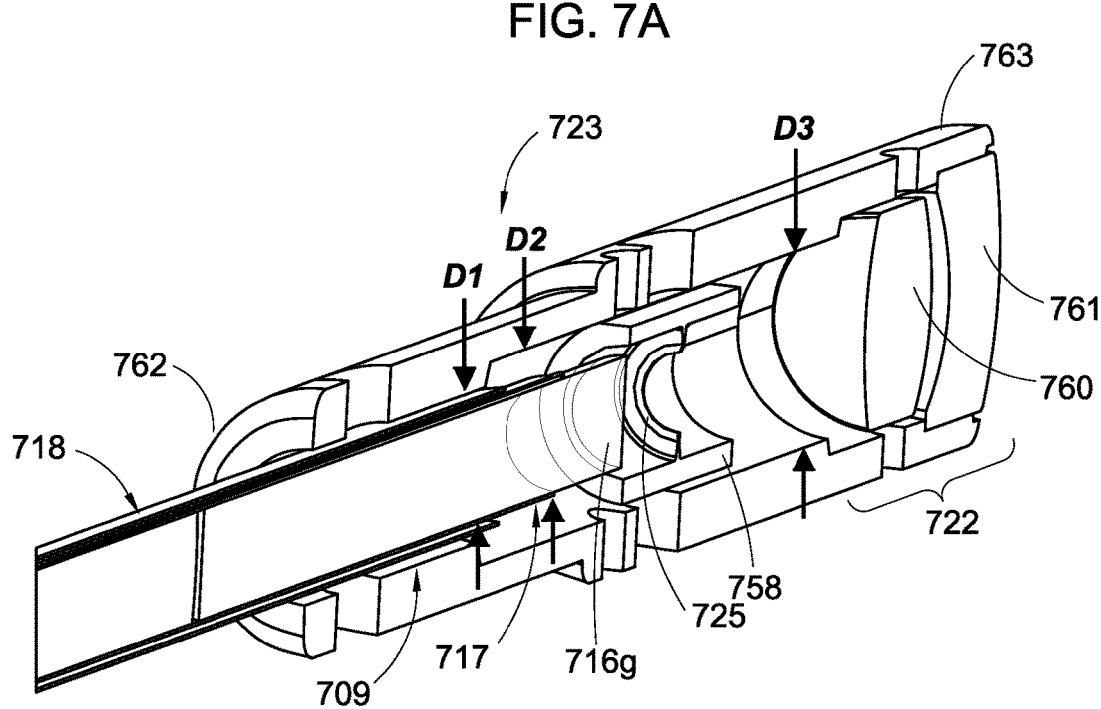
FIG. 7B illustrates a close-up three-dimensional cross-sectional view of the support structure of the optical joint which supports the connection between the proximal end of the insert portion comprising the protective tube, the lens tube having conductive member thereon and the optics therein, with the view port.

FIG. 7A illustrates a close-up cross-sectional view of the optical joint section 707 of an example endoscope such as shown in FIG. 6. In this example design, the proximal end 709 of the insert portion is received by a support structure 723 that mechanically stabilizes the distal end of the insert portion and may align the most proximal rod lens 716g enclosed in the lens tube 517, 217 (e.g., the optical axis of the last rod lens) with an eyepiece 722 (e.g., an optical axis thereof) enclosed in the support structure 723. FIG. 7B illustrates a 3D cross-sectional view of the support structure 723 wherein the proximal end 709 of the elongated member 414 is inserted. The support structure 723 has a distal end 762, a proximal end 763 and an internal cavity. The said distal end 762 may receive the proximal end 709 of the elongated member 414 and the said proximal end 763 houses the eyepiece 722. The diameter of the said internal cavity may vary along the longitudinal direction (parallel to the lens tube 717), in a stepwise manner from a first diameter D1 near the distal end 762 to a second diameter D2 somewhere in the middle and a third diameter D3 near the proximal end 763. The magnitude of the first diameter D1 may be equal to the magnitude of the outer diameter of the protective tube 718 such that the proximal end of the protective tube 709 fits therein so as to make a robust connection. The magnitude of the third diameter D3 may be equal to the magnitude of the diameter of the said eyepiece 722 (and therefore the diameter of the lenses therein). In some designs, the second diameter D2 may have a magnitude between those of the first and second diameter. The support structure 723 includes a field stop element 758 positioned in the middle of its internal cavity. The field stop element 758 may comprise a tube with an outer diameter equal to the second diameter D2 of the support structure and a non-transparent or opaque surface 725 in the middle of its internal cavity with an aperture (e.g., a circular aperture) provided at its center. This surface 725 and aperture can be located between the last rod lens 716g of the insert portion and the eyepiece 722 at a location where an image of the target region inside the patient's body is formed (e.g., the image plane of the imaging system comprising the optical components enclosed in the tip member 612 and the lens tube 717). Accordingly, the non-transparent or opaque surface and the aperture 725 therein may comprise a field stop. This surface 725 may be formed from black opaque plastic or metal.

In some implementations, the non-transparent or opaque surface defining the aperture 725 may be formed from a material that blocks light having a wavelength between 400 nm-1500 nm. The field stop element 758 and the non-transparent or opaque surface 725 may be formed from the same material. For example, they may be formed from various metals such as brass, aluminum, stainless steel. The non-transparent or opaque surface and the inner surfaces of the field stop element may be covered by an optically absorbing coating that absorbs the light incident thereon, at least, within 400 nm-1000 nm wavelength range.

The optical components enclosed in the tip member 612 and the lens tube 717 may generate a near aberration free image of a target region. The image can be a real image formed in the vicinity of the exit surface of the most proximal rod lens 716g. As discussed above, the relative distance between last the most proximal rod lens 716g and the surface 725 having the aperture therein may be selected such that the said real image is formed at that location and the aperture operates as a field stop. The light forming an image at the field stop may reach the eyepiece 722 resulting in formation of a final virtual image of the target region than may be observed by the user through the eyecup. This virtual image may for example be located at infinity or a large distance away. The field stop may limit the field of view of the endoscope to a specific range (limiting the portion of the target region observed through the eyepiece). The eyepiece may comprise one or more lenses designed and arranged to transform the real image received from the lens tube, into a possibly magnified virtual image viewable by the eye of the user peering through the viewport. The resultant image may have reduced aberration. In some implementations, the magnification provided by the eyepiece may be between 5× and 10×, or 1× and 20×, or 20× and 30× or any range between any of these values.

In some designed such as shown, the eyepiece may comprise one or more positive lenses or lens groups. The eyepiece may comprises, for example, a double-convex lens 760 and a convex-concave lens 761 comprising of a transparent material that transmits light within the wavelength range 400 nm-1000 nm with negligible attenuation. The eyepiece lens or lenses may comprise the same or different material.

In some implementations, the eyepiece may be designed to form a real image that may or may not be magnified compared to the real image provided by the lens tube (and formed at the location of the field stop). In these embodiments, the eyecup 703 may be eliminated and an optoelectronic image sensor may be placed at the image plane of the eyepiece where the final real image is generated. The optoelectronic image sensor may convert the corresponding optical distribution on its surface into an electric signal that can be fed into a projector or display device. Other configurations may be used that facilitate imaging by a camera that includes a 2D image sensor array. In one such implementation, the camera may be coupled to the viewport or the eyecup to capture images of the target region. Other variations and configurations are possible.

EXAMPLES

Examples of an endoscope for imaging a target region within a body are described herein such as the examples enumerated below:

Part-1

Example 1: An endoscope for imaging a target region within a body, comprising:
  a tip member comprising one or more light emitting devices configured to direct illumination at least a portion of said target region, said tip member also comprising a front window disposed so as to receive light from said target region when said tip is in said body, said tip further comprising a prism for redirecting light transmitted through said front window;
  an elongated member having proximal and distal ends, said tip member at said distal end;
  a plurality of lenses disposed along an optical path in said elongated member so as to receive light from said prism that transmitted through said front window;
  wherein said tip member comprises a housing that supports said one or more light emitting devices and said prism, and said housing comprises copper or a copper alloy.

Example 2: The endoscope of Example 1, wherein said tip member comprises bronze.

Example 3: The endoscope of Example 1, wherein said tip member comprises brass.

Example 4: The endoscope of Example 1, wherein said tip member comprises a copper alloy.

Example 5: The endoscope of Example 1, wherein said tip member comprises copper and not bronze or brass.

Example 6: The endoscope of Example 1, wherein said tip member comprises copper and not a copper alloy.

Part-2

Example 1: An endoscope for imaging a target region within a body, comprising:
  a tip member comprising one or more light emitting devices configured to direct illumination to at least a portion of said target region, said tip member also comprising a front window disposed so as to receive light from said target region when said tip is in said body, said tip member further comprising a prism for redirecting light transmitted through said front window;
  an elongated member having proximal and distal end, said tip member at said distal end;
  a plurality of lenses disposed along an optical path in said elongated member so as to receive light from said prism that transmitted through said front window;
  an elongate conducting member comprising a plurality of conducting lines embedded in an insulating membrane disposed along said elongated member;
  wherein said light emitting device is disposed on said elongate conducting member.

Example 2: The endoscope of Example 1, wherein said light emitting device is embedded in said insulating membrane.

Example 3: The endoscope of Examples 1 or 2, wherein said light emitting device is at said distal end of said elongate conducting member.

Example 4: The endoscope of any of Examples 1-3, wherein said tip member comprises a housing having a light emitting device seat, and said light emitting device is disposed on said light emitting device seat.

Example 5: The endoscope of Examples 1-4, wherein said light emitting device has a portion that is not covered by said insulating membrane.

Example 6: The endoscope of any of Examples 1-5, wherein said elongated conducting member has a length, width and thickness, wherein said length is larger than said width and said width is larger than said thickness.

Example 7: The endoscope of Example 6, wherein said elongated conducting member comprises a flexible elongated conducting member configured to bend at least along its length.

Example 8: The endoscope of Examples 6 or 7, wherein said elongate conducting member comprises a flexible elongated conducting member configured to bend at least along its width.

Example 9: The endoscope of any of Examples 6-8, wherein said elongate conducting member has a curved cross-section across its width.

Example 10: The endoscope of any of Examples 6-9, wherein said elongate conducting member is configured to maintain a curved cross-section across its with when any bending force is removed.

Example 11: The endoscope of any of Examples 6-10, wherein said insulating membrane is configured to maintain a curved cross-section across said elongate conducting member when any bending force is removed.

Part-3

Example 1: An endoscope for imaging a target region within a body, comprising:
- a tip member comprising one or more light emitting devices configured to direct illumination at least a portion of said target region, said tip member also comprising a front window disposed so as to receive light from said target region when said tip is in said body, said tip further comprising a prism for redirecting light transmitted through said front window;
- an elongated member having proximal and distal ends, said tip member at said distal end;
- a plurality of lenses disposed along an optical path in said elongated member so as to receive light from said prism that transmitted through said front window;
- an elongate conducting member comprising a plurality of conducting lines embedded in an insulating membrane disposed along said elongated member, said elongated conducting member having a length, width and thickness, wherein said length is larger than said width and said width is larger than said thickness,
- wherein said elongate conducting member has a curved cross-section across its width.

Example 2: The endoscope of Example 1, wherein said elongate conducting member is configured to maintain a curved cross-section across its with when any bending force is removed.

Example 3: The endoscope of any of Examples 1-2, wherein said insulating membrane is configured to maintain a curved cross-section across said elongated conducting member when any bending force is removed.

Part-4

Example 1: An endoscope for imaging a target region within a body, comprising:
- a tip member comprising one or more light emitting devices configured to direct illumination at least a portion of said target region, said tip member also comprising a front window disposed so as to receive light from said target region when said tip is in said body, said tip further comprising a prism for redirecting light transmitted through said front window;
- an elongated member having proximal and distal ends, said tip member at said distal end;
- a plurality of lenses disposed along an optical path in said elongated member so as to receive light from said prism that is transmitted through said front window;
- wherein said tip member comprises a housing configured to support said prism and said tip member has a side wall with a first opening for inserting said prism.

Example 2: The endoscope of Example 1, wherein said first opening in said housing has a shape that is similar to that of a cross-section of said prism.

Example 3: The endoscope of Example 1, wherein said first opening in said housing has a shape that is that similar to that of a sagittal cross-section of said prism.

Example 4: The endoscope of any of Examples 1-3, further comprising a second opening in a sidewall of said housing opposite to the first opening.

Example 5: The endoscope of Example 4, wherein said second opening has a shape that is the same as the shape of said first opening.

Example 6: The endoscope of any of Examples 4 or 5, wherein said second opening in said housing has a shape that is similar to that of a cross-section of said prism.

Example 7: The endoscope of any of Examples 4 or 5, wherein said second opening in said housing has a shape that is that similar to that of a sagittal cross-section of said prism.

Example 8: The endoscope of any of Examples 1-7, wherein said housing further comprises a cavity for said prism to be held in said housing.

Example 9: The endoscope of any of Examples 1-8, wherein said housing further includes an opening for light from said front window to pass into said housing and an opening for light from said window to exit said housing.

Example 10: The endoscope of any of Examples 1-9, wherein said housing further includes an opening for light from said front window to pass into said prism and an opening for light from said front window to exit said prism.

Example 11: The endoscope of any of Examples 1-10, wherein further comprising a first insert in said first opening.

Example 12: The endoscope of Example 11, wherein said first insert has a shape similar to said first opening.

Example 13: The endoscope of any of Examples 4-7, wherein further comprising second insert in said second opening.

Example 14: The endoscope of Example 13, wherein said second insert has a shape similar to said second opening.

Part-5

Example 1: An endoscope for imaging a target region within a body, comprising:
- a tip member comprising one or more light emitting devices configured to direct illumination at least a portion of said target region, said tip member also comprising a front window disposed so as to receive light from said target region when said tip is in said body, said tip further comprising a prism for redirecting light transmitted through said front window, said tip member comprising a housing that supports said one or more light emitting devices, said front window, and said prism;
- an elongated member having proximal and distal ends, said tip member at said distal end;
- a plurality of lenses disposed along an optical path in said elongated member so as to receive light from said prism that transmitted through said front window;
- a lens tube including at some of said lenses therein;
- a spacer configured to connect said lens tube to said housing of said tip member.

Example 2: The endoscope of Example 1, wherein said spacer comprises a distal portion and a proximal portion, wherein said distal portion of said spacer interfaces with said housing and wherein said proximal portion of said spacer interfaces with said lens tube.

Example 3: The endoscope of Example 2, wherein said housing receives said distal portion of said spacer.

Example 4: The endoscope of any of Examples 2-3, wherein said distal portion of said spacer has a smaller outer diameter than said proximal portion of said spacer.

Example 5: The endoscope of any of Examples 2-4, wherein said housing comprises a spacer seat and said distal portion of said spacer fits into said spacer seat.

Example 6: The endoscope of any of Examples 2-5, wherein said distal portion of said spacer has an outer diameter that matches an inner diameter of the spacer seat of said housing.

Example 7: The endoscope of any of Examples 2-6, wherein said proximal portion of said spacer has an outer diameter that matches an inner diameter of said lens tube.

Example 8: The endoscope of any of Examples 2-6, further comprising a protective tube that fits over said lens tube and said spacer.

Example 9: The endoscope of Example 8, wherein said a protective tube has an inner diameter larger than the width of said spacer.

Example 10: The endoscope of Example 8 or 9, wherein said protective tube fits over at least a portion of said housing.

Example 11: The endoscope of any of Examples 2-10, further comprising a rear lens disposed in said housing between said prism and said plurality of lenses.

Example 12: The endoscope of any of Examples 2-10, further comprising a rear lens disposed in said housing between said prism and said lenses in said lens tube.

Example 13: The endoscope of any of Examples 2-10, further comprising a rear lens disposed in said housing between said prism and said lens tube.

Example 14: The endoscope of any of Examples 11-13, further comprising an optical aperture disposed between said prism and said rear lens.

Example 15: The endoscope of any of Examples 11-13, wherein said housing includes a lens seat, said rear lens is disposed on said lens seat.

Example 16: The endoscope of Example 15, wherein said lens seat has a diameter smaller than a spacer seat for receiving said distal portion of said spacer.

Example 17: The endoscope of any of Examples 11-16, wherein said distal end of said lens tube contacts a proximal surface of said rear lens.

Example 18: The endoscope of any of Examples 11-17, wherein said spacer laterally aligns said lenses in said lens tube with said rear lens.

Example 19: The endoscope of any of Examples 11-18, wherein said spacer laterally aligns an optical axis said lenses in said lens tube with an optical axis of said rear lens.

Example 20: The endoscope of any of Examples 11-19, wherein said spacer establishes a longitudinal separation between said rear lens and the distal most lens in said lens tube.

Example 21: The endoscope of any of Examples 1-20, wherein said spacer comprises copper.

Example 22: The endoscope of any of Examples 1-20, wherein said spacer comprises a copper alloy.

Example 23: The endoscope of any of Examples 1-20, wherein said spacer comprises a bronze.

Example 24: The endoscope of any of Examples 1-20, wherein said spacer comprises a brass.

Example 25: The endoscope of any of Examples 1-24, wherein said housing of said tip member comprises copper.

Example 26: The endoscope of any of Examples 1-24, wherein said housing of said tip member comprises a copper alloy.

Example 27: The endoscope of any of Examples 1-24, wherein said housing of said tip member comprises bronze.

Example 28: The endoscope of any of Examples 1-24, wherein said housing of said tip member comprises brass.

Part-6

Example 1: An endoscope for imaging a target region within a body, comprising:
 a tip member comprising one or more light emitting devices configured to direct illumination at least a portion of said target region, said tip member also comprising a front window disposed so as to receive light from said target region when said tip is in said body, said tip member further comprising a prism for redirecting light transmitted through said front window;
 an elongated member having proximal and distal ends, said tip member at said distal end;
 a plurality of lenses disposed along an optical path in said elongated member so as to receive light from said prism that transmitted through said front window;
 a plurality of non-glass spacers between individual ones of said lenses to establish spacing therebetween.

Example 2: The endoscope of Example 1, wherein said non-glass spacers comprise a copper alloy.

Example 3: The endoscope of Example 1, wherein said non-glass spacers comprise brass.

Example 4: The endoscope of Example 1, wherein said non-glass spacers comprise bronze.

Example 5: The endoscope of Example 1, wherein said non-glass spacers comprise copper.

Example 6: The endoscope of Example 1, wherein said non-glass spacers comprises copper and not a copper alloy.

Example 7: The endoscope of any of Examples 1-6, wherein said tip member comprises a housing comprising copper.

Example 8: The endoscope of any of Examples 1-6, wherein said tip member comprises a housing comprising a copper alloy.

Example 9: The endoscope of any of Examples 1-6, wherein said tip member comprises a housing comprising bronze.

Example 10: The endoscope of any of Examples 1-6, wherein said tip member comprises a housing comprising brass.

Example 11: The endoscope of any of Examples 1-10, wherein said non-glass spacers comprise o-rings.

Part-7

Example 1: An endoscope for imaging a target region within a body, comprising:
 a tip member comprising one or more light emitting devices configured to direct illumination at least a portion of said target region, said tip member also comprising a front window disposed so as to receive light from said target region when said tip is in said body, said tip member further comprising a prism for redirecting light transmitted through said front window;
 an elongated member said elongated member having proximal and distal end, said tip member at said distal end
 a plurality of lenses disposed along an optical path in said elongated member so as to receive light from said prism that is transmitted through said front window,
 wherein said plurality of lenses disposed in said elongated member comprise no more than three different transparent lens materials.

Example 2: The endoscope of Example 1, wherein said plurality of lenses in said elongated member comprise no more than three different transparent lens glasses.

Example 3: The endoscope of Example 1, wherein plurality of lenses disposed in said elongated member together with said front lens in said tip member comprise no more than three different transparent lens materials.

Example 4: The endoscope of Example 1 or 3, wherein plurality of lenses disposed in said elongated member together with said front lens in said tip member comprise no more than three different transparent lens glasses.

Example 5: The endoscope of Example 1, wherein plurality of lenses disposed in said elongated member together with said front lens and said prism in said tip member comprise no more than three different transparent lens materials.

Example 6: The endoscope of Example 1 or 5, wherein plurality of lenses disposed in said elongated member together with said front lens and said prism in said tip member comprise no more than three different transparent lens glasses.

Example 7: The endoscope of Example 1, wherein plurality of lenses disposed in said elongated member together with said front lens, said prism, and a rear lens in said tip member comprise no more than three different transparent lens materials.

Example 8: The endoscope of Example 1 or 7, wherein plurality of lenses disposed in said elongated member together with said front lens, said prism, and said rear lens in said tip member comprise no more than three different transparent lens glasses.

Example 9: The endoscope of Example 1, wherein plurality of lenses disposed in said elongated member together with said front lens and a rear lens in said tip member comprise no more than three different transparent lens materials.

Example 10: The endoscope of Example 1 or 9, wherein plurality of lenses disposed in said elongated member together with said front lens and said rear lens in said tip member comprise no more than three different transparent lens glasses.

Example 11: The endoscope of any of Examples 1-10, further comprising at least one unpowered rod in said elongated member.

Example 12: The endoscope of Example 11, wherein said plurality of lenses and said at least one unpowered rod disposed in said elongated member comprise no more than three different transparent lens materials.

Example 13: The endoscope of Example 11 or 12, wherein said plurality of lenses and said at least one unpowered rod in said elongated member comprise no more than three different transparent lens glasses.

Example 14: The endoscope of Example 11, wherein said plurality of lenses and said at least one unpowered rod disposed in said elongated member together with said front lens in said tip member comprise no more than three different transparent lens materials.

Example 15: The endoscope of Example 11 or 14, wherein said plurality of lenses and said at least one unpowered rod in said elongated member together with said front lens in said tip member comprise no more than three different transparent lens glasses.

Example 16: The endoscope of Example 11, wherein said plurality of lenses and said at least one unpowered rod disposed in said elongated member together with said front lens and said prism in said tip member comprise no more than three different transparent lens materials.

Example 17: The endoscope of Example 11 or 16, wherein said plurality of lenses and said at least one unpowered rod in said elongated member together with said front lens and said prism in said tip member comprise no more than three different transparent lens glasses.

Example 18: The endoscope of Example 1, wherein said plurality of lenses and said at least one unpowered rod disposed in said elongated member together with said front lens and a rear lens in said tip member comprise no more than three different transparent lens materials.

Example 19: The endoscope of Example 1 or 18, wherein said plurality of lenses and said at least one unpowered rod in said elongated member together with said front lens and a rear lens in said tip member comprise no more than three different transparent lens glasses.

Example 20: The endoscope of Example 1, wherein said plurality of lenses and said at least one unpowered rod disposed in said elongated member together with said front lens, said prism, and a rear lens in said tip member comprise no more than three different transparent lens materials.

Example 21: The endoscope of Example 1 or 20, wherein said plurality of lenses and said at least one unpowered rod in said elongated member together with said front lens, said prism, and a rear lens in said tip member comprise no more than three different transparent lens glasses.

Example 22: The endoscope of any of Examples 1-21, wherein any one of said lenses includes an optical coating thereon.

Example 23: The endoscope of Example 22, wherein said optical coating comprises different material than said lenses on which it is deposited.

Example 24: The endoscope of Example 22, wherein said optical coating comprises an anti-reflective coating.

Example 25: The endoscope of any of Examples 1-24, wherein the number of lenses in said elongated member comprises at least 4.

Example 26: The endoscope of any of Examples 1-24, wherein the number of lenses in said elongated member comprises at least 5.

Example 27: The endoscope of any of Examples 1-24, wherein the number of lenses in said elongated member comprises at least 6.

Example 28: The endoscope of any of Examples 1-24, wherein the number of lenses in said elongated member comprises at least 7.

Example 29: The endoscope of any of Examples 1-28, wherein the number of rod lenses in said elongated member comprises at least 3.

Example 30: The endoscope of any of Examples 1-28, wherein the number of lenses in said elongated member comprises at least 4.

Example 31: The endoscope of any of Examples 1-28, wherein the number of lenses in said elongated member comprises at least 5.

Example 32: The endoscope of any of Examples 1-28, wherein the number of lenses in said elongated member comprises at least 6.

Part-8

Example 1: An endoscope for imaging a target region within a body, comprising:
  a tip member comprising one or more light emitting devices configured to direct illumination at least a portion of said target region, said tip member also comprising a front window disposed so as to receive light from said target region when said tip is in said body, said tip member further comprising a prism for redirecting light transmitted through said front window;
  an elongated member having proximal and distal ends, said tip member at said distal end;
  a plurality of lenses disposed along an optical path in said elongated member so as to receive light from said prism that is transmitted through said front window,
  wherein said plurality of lenses disposed in said elongated member comprise no more than eight lenses.

Example 2: The endoscope of Example 1, wherein said elongated member comprise no more than seven lenses.

Example 3: The endoscope of Examples 1 or 2, further comprising an unpowered rod in said elongated member.

Example 4: The endoscope of Examples 1 or 2, further comprising one and only one unpowered rod in said elongated member.

Example 5: The endoscope of any of Examples 1-4, wherein said plurality of lenses in said elongated element comprises one and only one doublet formed from two of said lens.

Example 6: The endoscope of Example 5, wherein said doublet provides chromatic correction.

Example 7: The endoscope of Example 5 or 6, wherein said doublet has an aspheric surface.

Example 8: The endoscope of Examples 7, wherein said aspheric surface on said doublet is on the most proximal optical surface of doublet.

Example 9: The endoscope of any of Examples 1-6, further comprising one and only one aspheric optical surface in said elongated member.

Example 10: The endoscope of any of the above Examples, wherein said elongated member is from 5 cm to 25 cm long.

Example 11: The endoscope of any of the above Examples, wherein said plurality of lenses are included in a lens tube in said elongated.

Example 12: The endoscope of any of Examples 1-12, wherein the number of lenses in said elongated member comprises at least 4.

Example 13: The endoscope of any of Examples 1-12, wherein the number of lenses in said elongated member comprises at least 5.

Example 14: The endoscope of any of Examples 1-12, wherein the number of lenses in said elongated member comprises at least 6.

Example 15: The endoscope of any of Examples 1-21, wherein the number of lenses in said elongated member comprises at least 7.

Example 16: The endoscope of any of Examples 1-16, wherein the number of rod lenses in said elongated member comprises at least 3.

Example 17: The endoscope of any of Examples 1-16, wherein the number of lenses in said elongated member comprises at least 4.

Example 18: The endoscope of any of Examples 1-16, wherein the number of lenses in said elongated member comprises at least 5.

Example 19: The endoscope of any of Examples 1-16, wherein the number of lenses in said elongated member comprises at least 6.

Example 20: The endoscope of any of the above Examples, wherein said elongated member is from 10 cm to 20 cm long.

Part-9

Example 1: An endoscope for imaging a target region within a body, comprising:
- a tip member comprising one or more light emitting devices configured to direct illumination at least a portion of said target region, said tip member also comprising a front window disposed so as to receive light from said target region when said tip is in said body, said tip member further comprising a prism for redirecting light transmitted through said front window;
- an elongated member having proximal and distal ends, said tip member at said distal end; and
- a plurality of lenses disposed along an optical path in said elongated member so as to receive light from said prism that is transmitted through said front window,
- an eyepiece or camera, light from said target region collected by said front lens propagating along an optical path from said front lens through said prism and said plurality of lens in said elongated member forming a real image that is viewable through said eyepiece or camera;
- wherein no more than ten lenses extend along an optical path from said front lens to said real image.

Example 2: The endoscope of Example 1, wherein no more than nine lenses extend along an optical path from said front lens to said real image.

Example 3: The endoscope of Examples 1 or 2, further comprising an unpowered rod in elongated member.

Example 4: The endoscope of Examples 1 or 2, further comprising one and only one unpowered rod in said optical path from said front lens to said real image.

Example 5: The endoscope of any of Examples 1-4, wherein one and only one doublet formed from two of said lens is in said optical path from said front lens to said real image.

Example 6: The endoscope of Example 5, wherein said doublet provides chromatic correction.

Example 7: The endoscope of Example 5 or 6, wherein said doublet has an aspheric surface.

Example 8: The endoscope of Example 7, wherein said aspheric surface on said doublet is on the most proximal optical surface of doublet.

Example 9: The endoscope of any of Examples 1-6, further comprising one and only one aspheric optical surface in said optical path from said front lens to said real image.

Example 10: The endoscope of any of the above Examples, wherein said plurality of lenses are included in a lens tube in said elongated member.

Example 11: The endoscope of any of Examples 1-12, wherein the number of lenses in optical path from said front lens to said real image comprises at least 6.

Example 12: The endoscope of any of Examples 1-12, wherein the number of lenses in optical path from said front lens to said real image comprises at least 7.

Example 13: The endoscope of any of Examples 1-12, wherein the number of lenses in optical path from said front lens to said real image comprises at least 8.

Example 14: The endoscope of any of Examples 1-12, wherein the number of lenses in optical path from said front lens to said real image comprises 9.

Example 15: The endoscope of any of Examples 1-16, wherein the number of rod lenses in said elongated member comprises at least 3.

Example 16: The endoscope of any of Examples 1-16, wherein the number of lenses in said elongated member comprises at least 4.

Example 17: The endoscope of any of Examples 1-16, wherein the number of lenses in said elongated member comprises at least 5.

Example 18: The endoscope of any of Examples 1-16, wherein the number of lenses in said elongated member comprises at least 6.

Part-10

Example 1: An endoscope for imaging a target region within a body, comprising:
- a tip member comprising one or more light emitting devices configured to direct illumination at least a portion of said target region, said tip member also comprising a front window disposed so as to receive light from said target region when said tip is in said body, said tip member further comprising a prism for redirecting light transmitted through said front window;

an elongated member having proximal and distal ends, said tip member at said distal end; and a plurality of lenses disposed along an optical path in said elongated member so as to receive light from said prism that is transmitted through said front window, an eyepiece, light from said target region collected by said front lens propagating along an optical path from said front lens through said prism and said plurality of lens in said elongated member to form an image viewable through said eyepiece;

wherein no more than ten lenses extend along an optical path from said front lens to said eyepiece.

Example 2: The endoscope of Example 1, wherein no more than nine lenses extend along an optical path from said front lens to said eyepiece.

Example 3: The endoscope of Examples 1 or 2, further comprising an unpowered rod in said optical path from said front lens to said eyepiece.

Example 4: The endoscope of Examples 1 or 2, further comprising one and only one unpowered rod in said optical path said front lens to said eyepiece.

Example 5: The endoscope of any of Examples 1-4, wherein one and only one doublet is formed from two of said lens is in said optical path from said front lens to said eyepiece.

Example 6: The endoscope of Example 5, wherein said doublet provides chromatic correction.

Example 7: The endoscope of Example 5 or 6, wherein said doublet has an aspheric surface.

Example 8: The endoscope of Example 7, wherein said aspheric surface on said doublet is on the most proximal optical surface of doublet.

Example 9: The endoscope of any of Examples 1-6, further comprising one and only one aspheric optical surface in said optical path from said front lens to said eyepiece.

Example 10: The endoscope of any of the above Examples, wherein said plurality of lenses are included in a lens tube in said elongated member.

Example 11: The endoscope of any of Examples 1-12, wherein the number of lenses in optical path from said front lens to said eyepiece comprises at least 6.

Example 12: The endoscope of any of Examples 1-12, wherein the number of lenses in optical path from said front lens to said eyepiece comprises at least 7.

Example 13: The endoscope of any of Examples 1-12, wherein the number of lenses in optical path from said front lens to said eyepiece comprises at least 8.

Example 14: The endoscope of any of Examples 1-12, wherein the number of lenses in optical path from said front lens to said eyepiece comprises 9.

Example 15: The endoscope of any of Examples 1-16, wherein the number of rod lenses in said elongated member comprises at least 3.

Example 16: The endoscope of any of Examples 1-16, wherein the number of lenses in said elongated member comprises at least 4.

Example 17: The endoscope of any of Examples 1-16, wherein the number of lenses in said elongated member comprises at least 5.

Example 18: The endoscope of any of Examples 1-16, wherein the number of lenses in said elongated member comprises at least 6.

Part-11

Example 1: An endoscope for imaging a target region within a body, comprising:

a tip member comprising one or more light emitting devices configured to direct illumination at least a portion of said target region, said tip member also comprising a front window disposed so as to receive light from said target region when said tip is in said body, said tip member further comprising a prism for redirecting light transmitted through said front window;

an elongated member having proximal and distal ends, said tip member at said distal end;

a plurality of lenses disposed along an optical path in said elongated member so as to receive light from said prism that is transmitted through said front window; and a camera, light from said target region collected by said front lens propagating along an optical path from said front lens through said prism and said plurality of lens in said elongated member to form an image viewable through said camera;

wherein no more than ten lenses extend along an optical path from said front lens to said camera.

Example 2: The endoscope of Example 1, wherein no more than nine lenses extend along an optical path from said front lens to said camera.

Example 3: The endoscope of Examples 1 or 2, further comprising an unpowered rod in said optical path from said front lens to said camera.

Example 4: The endoscope of Examples 1 or 2, further comprising one and only one unpowered rod in said optical path said front lens to said camera.

Example 5: The endoscope of any of Examples 1-4, wherein one and only one doublet formed from two of said lens is in said optical path from said front lens to said camera.

Example 6: The endoscope of Example 5, wherein said doublet provides chromatic correction.

Example 7: The endoscope of Example 5 or 6, wherein said doublet has an aspheric surface.

Example 8: The endoscope of Example 7, wherein said aspheric surface on said doublet is on the most proximal optical surface of doublet.

Example 9: The endoscope of any of Examples 1-6, further comprising one and only one aspheric optical surface in said optical path from said front lens to said camera.

Example 10: The endoscope of any of Examples 1-10, wherein the number of lenses in optical path from said front lens to said camera comprises at least 6.

Example 11: The endoscope of any of Examples 1-10, wherein the number of lenses in optical path from said front lens to said camera comprises at least 7.

Example 12: The endoscope of any of Examples 1-10, wherein the number of lenses in optical path from said front lens to said camera comprises at least 8.

Example 13: The endoscope of any of Examples 1-10, wherein the number of lenses in optical path from said front lens to said camera comprises 9.

Example 14: The endoscope of any of Examples 1-14, wherein the number of rod lenses in said elongated member comprises at least 3.

Example 15: The endoscope of any of Examples 1-14, wherein the number of lenses in said elongated member comprises at least 4.

Example 16: The endoscope of any of Examples 1-14, wherein the number of lenses in said elongated member comprises at least 5.

Example 17: The endoscope of any of Examples 1-14, wherein the number of lenses in said elongated member comprises at least 6.

What is claimed is:

1. An endoscope for imaging a target region within a body, comprising:
   a tip member comprising:
      one or more light emitting devices configured to direct illumination to at least a portion of said target region,
      a front window disposed so as to receive light from said target region when said tip member is in said body,
      a prism for redirecting light transmitted through said front window;
      a housing that supports said one or more light emitting devices and said prism, and
      a side wall with a first opening for inserting said prism;
   an elongated member having proximal and distal ends, said tip member at said distal end;
   a plurality of lenses disposed along an optical path in said elongated member so as to receive light from said prism that is transmitted through said front window;
   an elongated conducting member comprising a plurality of conducting lines embedded in an insulating membrane disposed along said elongated member;
   wherein said one or more light emitting devices are disposed on said elongated conducting member.

2. The endoscope of claim 1, wherein said one or more light emitting devices are embedded in said insulating membrane.

3. The endoscope of claim 1, wherein said one or more light emitting devices are at said distal end of said elongated conducting member.

4. The endoscope of claim 1, wherein said housing of said tip member has a light emitting device seat, and said one or more light emitting devices are disposed on said light emitting device seat.

5. The endoscope of claim 1, wherein said one or more light emitting devices have a portion that is not covered by said insulating membrane.

6. The endoscope of claims 1, wherein said elongated conducting member has a length, width and thickness, wherein said length is larger than said width and said width is larger than said thickness.

7. The endoscope of claim 6, wherein said elongated conducting member comprises a flexible elongated conducting member configured to bend at least along its length.

8. The endoscope of claims 7, wherein said elongated conducting member comprises a flexible elongated conducting member configured to bend at least along its width.

9. The endoscope of claims 8, wherein said elongated conducting member has a curved cross-section across its width.

10. The endoscope of claims 9, wherein said elongated conducting member is configured to maintain a curved cross-section across its width when any bending force is removed.

11. The endoscope of claims 9, wherein said insulating membrane is configured to maintain a curved cross-section across said elongated conducting member when any bending force is removed.

12. The endoscope of claim 1, wherein said first opening in said housing has a shape that is similar to that of a cross-section of said prism.

13. The endoscope of claim 1, wherein said tip member comprises bronze.

14. The endoscope of claim 1, wherein said tip member comprises brass.

15. The endoscope of claim 1, wherein said tip member comprises copper or a copper alloy.

* * * * *